(12) United States Patent
Liu et al.

(10) Patent No.: US 12,409,135 B2
(45) Date of Patent: Sep. 9, 2025

(54) NEOEPITOPE VACCINE DELIVERY VEHICLE AND METHODS OF MAKING THE SAME

(71) Applicant: ImmunityBio, Inc., Culver City, CA (US)

(72) Inventors: Philip T. Liu, Culver City, CA (US); Clifford Anders Olson, Culver City, CA (US); Wade Nichols Richardson, Culver City, CA (US); Wendy Higashide, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

(21) Appl. No.: 18/062,416

(22) Filed: Dec. 6, 2022

(65) Prior Publication Data

US 2023/0172852 A1    Jun. 8, 2023

Related U.S. Application Data

(60) Provisional application No. 63/287,176, filed on Dec. 8, 2021.

(51) Int. Cl.

| | | |
|---|---|---|
| A61K 9/06 | (2006.01) | |
| A61K 38/06 | (2006.01) | |
| A61K 41/00 | (2020.01) | |
| A61K 47/36 | (2006.01) | |
| C12N 15/10 | (2006.01) | |
| C12N 15/87 | (2006.01) | |

(52) U.S. Cl.
CPC .............. *A61K 9/06* (2013.01); *A61K 38/063* (2013.01); *A61K 41/0028* (2013.01); *A61K 47/36* (2013.01); *C12N 15/1055* (2013.01); *C12N 15/87* (2013.01)

(58) Field of Classification Search
CPC .......... A61K 9/06; A61K 47/36; A61K 47/61; A61K 47/6939; A61K 38/063; A61K 2039/55583; C12N 15/1055; C12N 15/87
USPC ........................................................ 514/23
See application file for complete search history.

(56) References Cited

U.S. PATENT DOCUMENTS

| | | | |
|---|---|---|---|
| 5,853,737 A | 12/1998 | Modlin et al. | |
| 6,238,676 B1 | 5/2001 | Porcelli et al. | |
| 8,759,322 B2 | 6/2014 | Akiyoshi et al. | |
| 8,961,983 B2 | 2/2015 | Akiyoshi et al. | |
| 8,987,230 B2 | 3/2015 | Akiyoshi et al. | |
| 9,205,103 B2 | 12/2015 | Portela Da Gama et al. | |
| 10,391,060 B2 | 8/2019 | Pilgaonkar et al. | |
| 2012/0029175 A1 | 2/2012 | Nagura et al. | |
| 2013/0045242 A1* | 2/2013 | Portela Da Gama | A61L 27/54 977/773 |
| 2015/0231268 A1 | 8/2015 | Nakai et al. | |
| 2017/0202789 A1 | 7/2017 | Sexton et al. | |
| 2019/0111078 A1 | 4/2019 | Shiku et al. | |
| 2019/0142960 A1 | 5/2019 | Haimovitz-Friedman et al. | |
| 2019/0351043 A1 | 11/2019 | Briles et al. | |
| 2021/0299061 A1 | 9/2021 | Malkoch et al. | |
| 2021/0322531 A1 | 10/2021 | Hayashi et al. | |
| 2022/0111061 A1* | 4/2022 | Harada .................. A61K 47/61 |

FOREIGN PATENT DOCUMENTS

| | | |
|---|---|---|
| CN | 110156911 | 8/2019 |
| FR | 2839517 | 11/2003 |
| FR | 3104951 | 6/2021 |
| JP | 2007-252304 | 10/2007 |
| JP | 4550555 B | 9/2010 |
| JP | 4599550 B | 12/2010 |
| JP | 2012232949 | 11/2012 |
| JP | 5866724 | 2/2016 |
| WO | WO 98/09650 | 3/1998 |
| WO | WO 00/020563 | 4/2000 |
| WO | WO 00/059948 | 10/2000 |
| WO | WO 02/076441 | 10/2002 |
| WO | WO 2007/119859 | 10/2007 |
| WO | WO 2013/160190 | 10/2013 |
| WO | WO 2014/054588 | 4/2014 |
| WO | WO 2014/157606 | 10/2014 |
| WO | WO 2015/119181 | 8/2015 |
| WO | WO 2017/170494 | 10/2017 |
| WO | WO 2020/027309 | 2/2020 |
| WO | WO 2020/045488 | 3/2020 |
| WO | WO 2020/203731 | 10/2020 |

OTHER PUBLICATIONS

Ojala et al., Published Jun. 2, 2000, Carbohydrate Research, vol. 326, Issue 2, pp. 104-112 (Year: 2000).*
Xu et al., Published Oct. 30, 2018, ACS Applied Materials & Interfaces, vol. 10, Issue 46, pp. 39494-39504 (Year: 2018).*
Wagh et al., Published Jan. 1, 2013, Methods for Conjugating Antibodies to Nanocarriers, in Ducry, L. Antibody-Drug Conjugates, (New York, Humana Press, 2013), pp. 249-266 (Year: 2013).*
Felber, M., Published Jan. 7, 2016, Ph.D. Dissertation, Universität Zürich, pp. 1-160, DOI: 10.5167/uzh-118686 (Year: 2016).*
Akiyama et al., Self-assembled nanogels of cholesteryl-modified polysaccharides: effect of the polysaccharide structure on their association characteristics in the dilute and semidilute regimes, Biomacromolecules, Jul. 14, 2007, vol. 8(8), pp. 2366-2373.
Ferreira et al., "Development of Multifunctional Mannan Nanogel," ProQuest LLC, ProQuest No. 10592490, Universidade do Minho, Thesis for PhD Degree in Biomedical Engineering, Apr. 2012, 4 pages, abstract only.
Ferreira et al., "Self-Assembled Mannan Nanogel: Cytocompatibility and Cell Localization," Journal of Biomedical Nanotechnology, 2012, vol. 8(3), pp. 1-9.

(Continued)

*Primary Examiner* — Renee Claytor
*Assistant Examiner* — Jaret J Crews
(74) *Attorney, Agent, or Firm* — Sheridan Ross P.C.

(57) ABSTRACT

Disclosed herein are mannan nanogels as a novel vaccine delivery platform as well as a novel method of making a self-assembling mannan nanogel for in vivo delivery of therapeutic agents.

7 Claims, 23 Drawing Sheets

Specification includes a Sequence Listing.

(56) References Cited

OTHER PUBLICATIONS

Ferreira et al., "Self-Assembled Nanogel Made of Mannan: Synthesis and Characterization," Langmuir, Jun. 2, 2010, 26(13), pp. 11413-11420.
Ferreira et al., "Supramolecular assembled nanogel made of mannan," Journal of Colloid and Interface Science, Sep. 1, 2011, vol. 361(1), pp. 97-108.
Ferreirs et al., "Polymeric nanogels as vaccine delivery systems," Nanomedicine: Nanotechnology, Biology and Medicine, Feb. 2013, vol. 9(2), pp. 159-173.
Grego et al., "Polymeric Nanoparticle-Based Vaccine Adjuvants and Delivery Vehicles," Current Topics in Microbiology and Immunology, Author Manuscript, 2021, vol. 433, pp. 29-76, 45 pages.
Gu, "A Novel Hydrophobized Polysaccharide/Oncoprotein Complex Vaccine Induces in Vitro and In Vivo Cellular and Humoral Immune Responses Against HER2-expressing Murine Sarcomas," Cancer Research, 1998, vol. 58(15), pp. 3385-3390.
Ikuta et al., "Presentation of a major histocompatibility complex class 1-binding peptide by monocyte-derived dendritic cells incorporating hydrophobized polysaccharide-truncated HER2 protein complex: implications for a polyvalent immuno-cell therapy," Blood, May 15, 2002, vol. 99(10), pp. 3717-3724.
Kang, "Specific Partition of Surface-Modified Liposomes in Aqueous PEO/Polysaccharide Two-Phase Systems," Adsorption and Aggregation of Surfactants in Solution, 1st Edition, 2003, vol. 109, pp. 520-542.
Lang et al., "Carbohydrate Conjugates in Vaccine Developments," Frontiers in Chemistry, Apr. 15, 2020, vol. 8(284), 1-25 pages.
Leber et al., "α-Mannosyl-Functionalized Cationic Nanohydrogel Particles for Targeted Gene Knockdown in Immunosuppressive Macrophages," Macromolecular Bioscience, Jul. 2019, vol. 19(7), e1900162, 12 pages.
Malik et al., "Efaverinz and nano-gold-loaded mannosylated niosomes: a host cell-targeted topical HIV-1 prophylaxis via thermogel system," Artificial Cells, Nanomedicine, and Biotechnology, 2018, vol. 46(S1), pp. S79-S90.
Miki et al., "Methylation-triggered fractionation of lignocellulosic biomass to afford cellulose-, hemicellulose-, and lignin-based functional polymers via click chemistry," Green Chemistry, Apr. 22, 2020, vol. 22, pp. 2909-2928.
Mutalabisin et al., "pH Responsive Polymers in Drug Delivery," Research Journal of Pharmacy and Technology, Nov. 2018, vol. 11(11), pp. 5115-5122.
Patel et al., "Recent Trends in Microbially and/or Enzymatically Driven Colon-Specific Drug Delivery Systems," Critical Reviews™M in Therapeutic Drug Carrier Systems, 2011, vol. 28(6), pp. 489-552.
Rodriguez et al., "The Surfaces of the *Ceratonia siliqua* L. (Carob) Leaflet: Insights from Physics and Chemistry," Langmuir, Feb. 3, 2021, vol. 37(6), pp. 2011-2028.
Shiku et al., "A Novel Hydrophobized Polysaccharide/Oncoprotein Complex Vaccine for HER2 Gene Expressing Cancer," Biomedical Polymers and Polymer Therapeutics, 2002, pp. 331-337.
Varshosaz et al., "Supramolecular Self-Assembled Nanogels a New Platform for Anticancer Drug Delivery," Current Pharmaceutical Design, 2017, vol. 23(35), pp. 5242-5260.
Vigerust et al., "Stable Expression and Characterization of an Optimized Mannose Receptor," Journal of Clinical & Cellular Immunology, 2015, vol. 6(3), 10 pages.
Yamane et al., "Hybrid Nanoapatite by Polysaccharide Nanogel-templated Mineralization," Journal of Bioactive and Compatible Polymers, Mar. 1, 2009, vol. 24(2), pp. 151-168.
Zhang et al., "Cholesteryl-Modification of a Glucomannan from *Bletilla striata* and Its Hydrogel Properties," Molecules, 2014, vol. 19, pp. 9089-9100.
International Search Report and Written Opinion for International (PCT) Application No. PCT/US2022/081025, dated Apr. 17, 2023 11 pages.

* cited by examiner

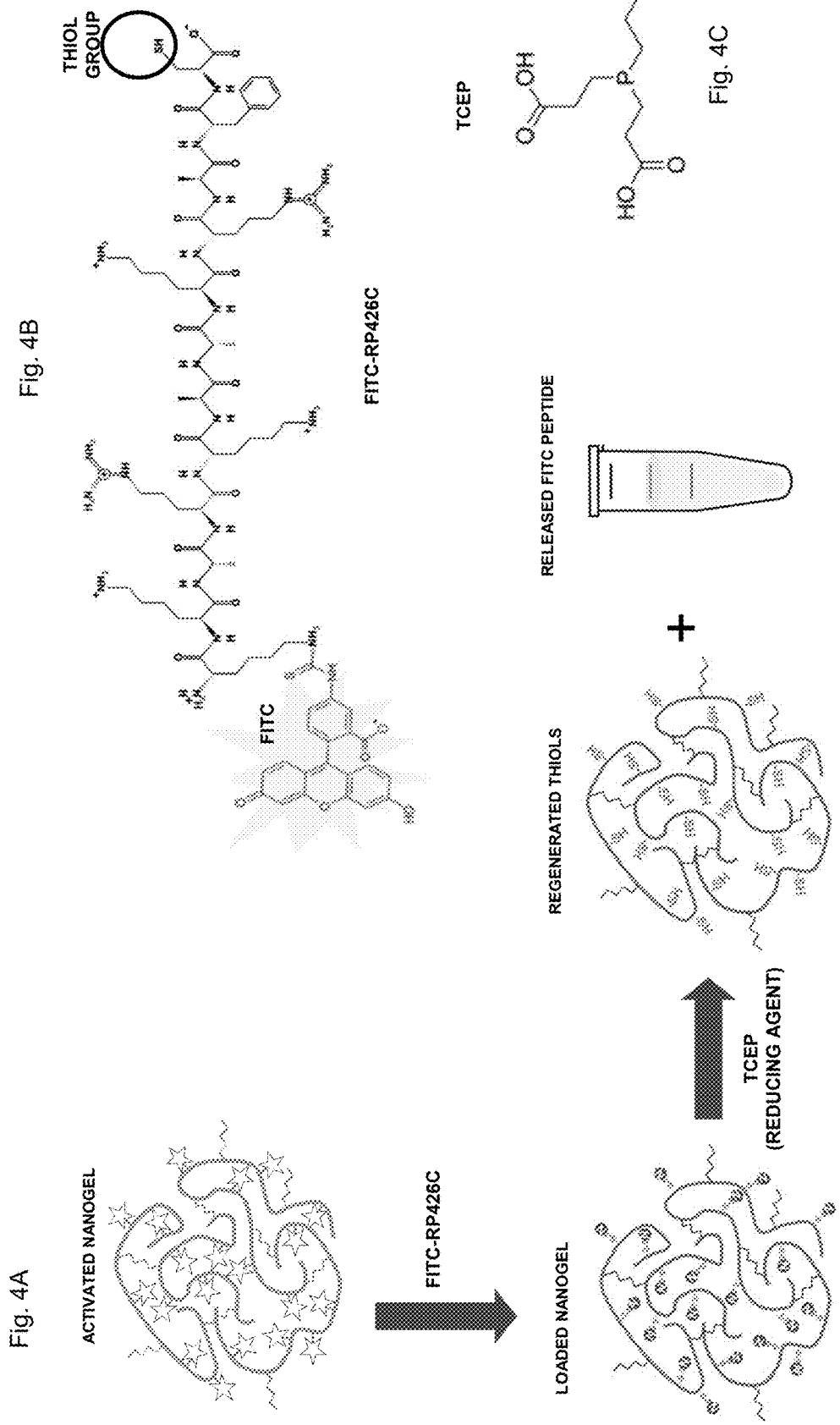

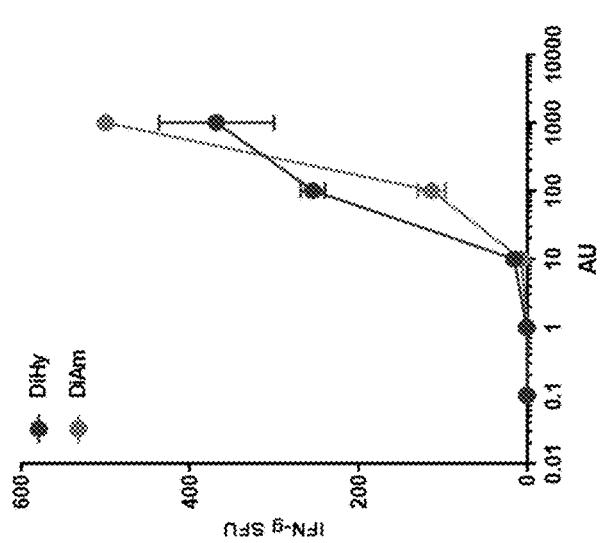
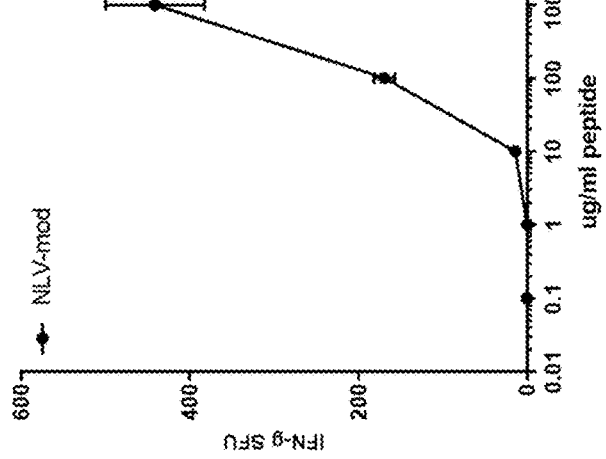
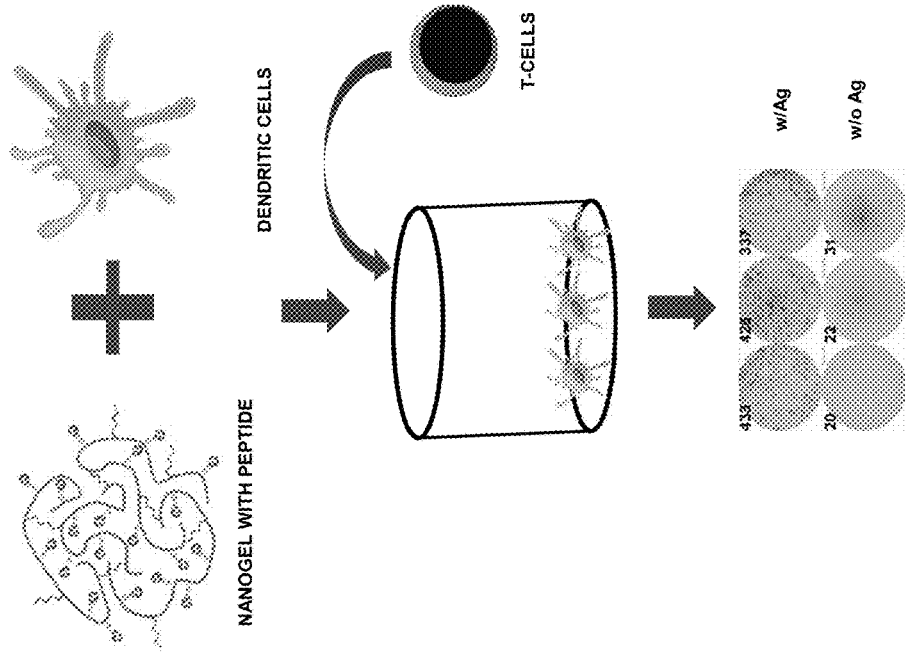

Glutathione (GSH)

NLV-mod antigen peptide

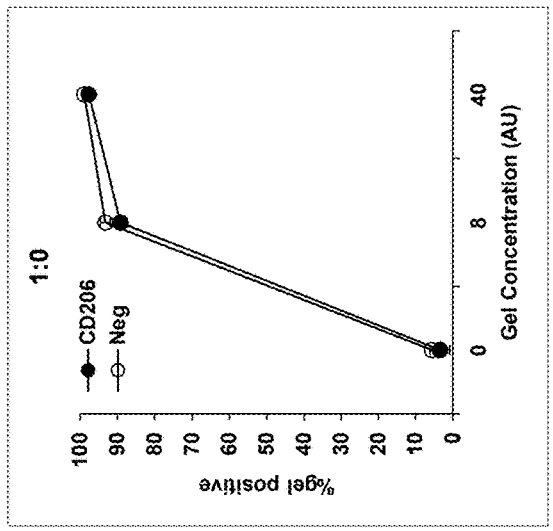
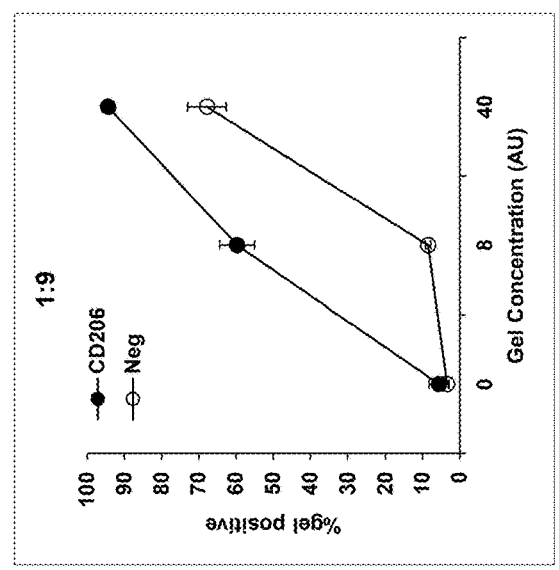
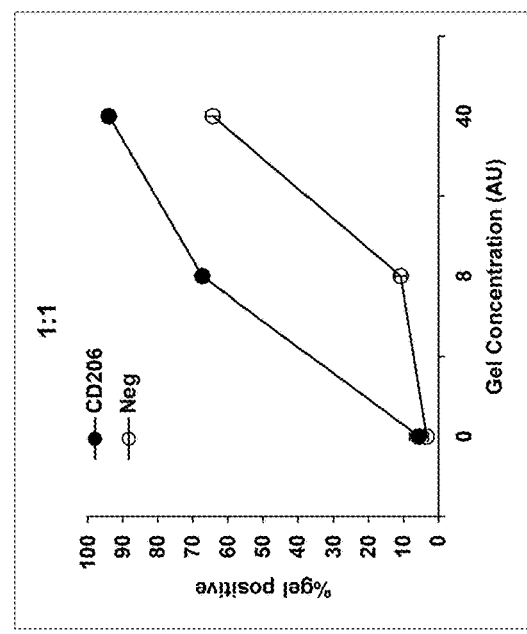
Fig. 14A
Fig. 14B
Fig. 14C

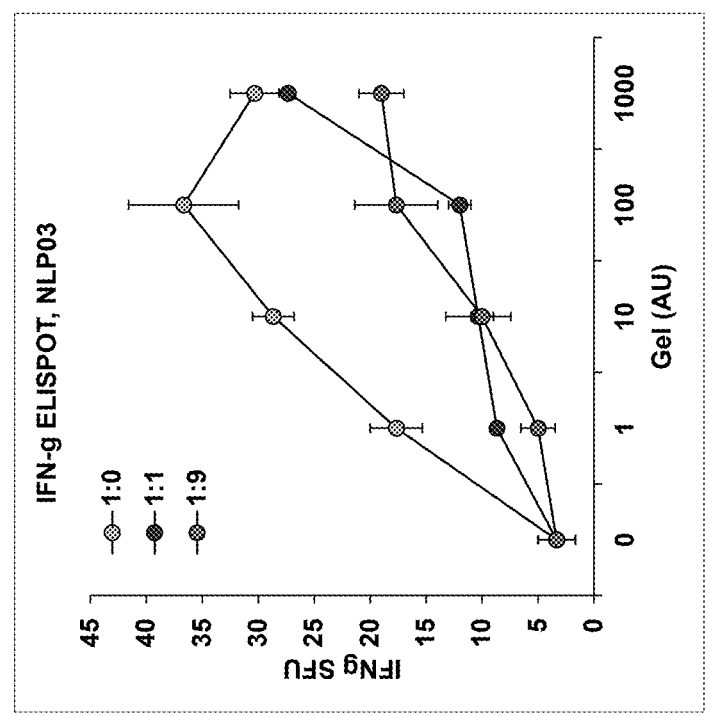

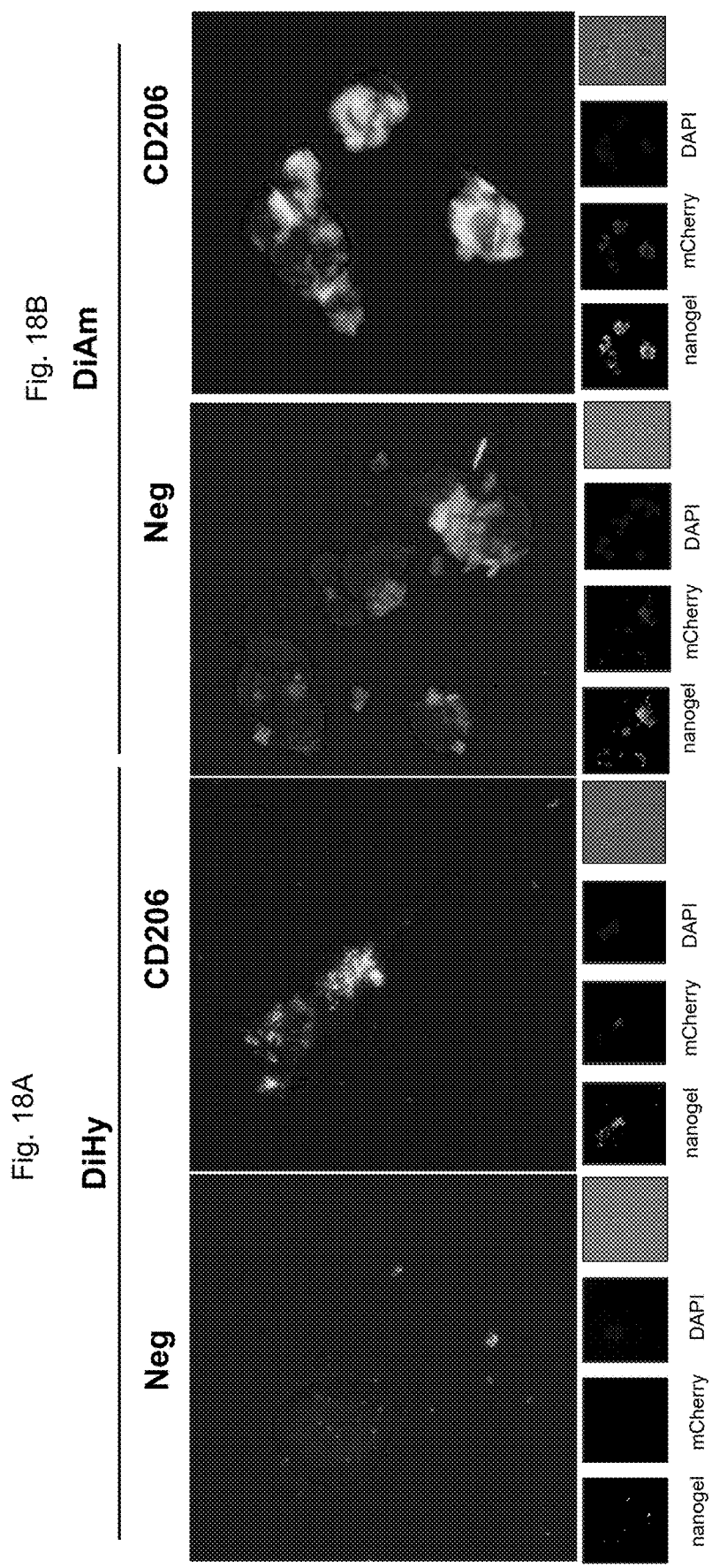
Fig. 18A DiHy
Fig. 18B DiAm
*Red exposure increased for DiHy

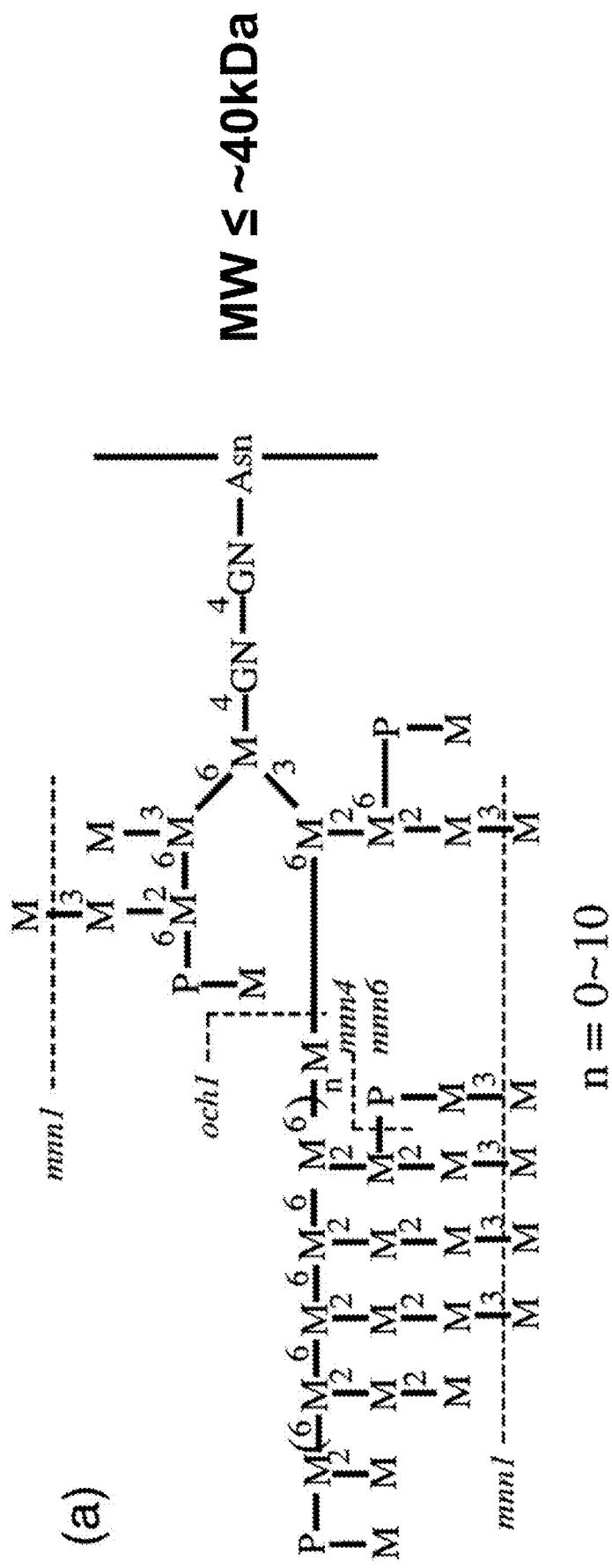

```
                            SEQUENCE LISTING

Sequence total quantity: 1
SEQ ID NO: 1            moltype = DNA  length = 4371
FEATURE                 Location/Qualifiers
source                  1..4371
                        mol_type = other DNA
                        organism = synthetic construct
SEQUENCE: 1
atgcggctgc ccctgctcct ggtgttcgcc agcgtgatcc ctggagctgt gctgctgctg    60
gatacccggc aatttcttat ctataacgag gaccacaagc ggtgcgtcga cgccgtgagc   120
ccaagcgccg tgcagaccgc cgcttgcaat caagacgacg aaagccaaaa gttcagatgg   180
gtgagcgaga gccagatcat gagcgtggcc ttcaagctgt gcctgggcgt gcctagcaag   240
accgattggg tcgctatcac tctgtacgcc tgcgacagca aaagcgagtt ccagaaatgg   300
gaatgcaaaa acgacacact tttgggcatc aagggcgagg acctgttctt caactacggc   360
aatagacagg agaagaacat catgctgtac aagggcgacg gcctgtggtc cagatggaag   420
atctacggca ccaccgacaa cctgtgtagc cggggctacg aggccatgta cacccctgtg   480
ggaaacgcga acgcgctac ctgcgccttc cccttttaagt tcgagaacaa gtggtacgct   540
gattgcacca gcgctggcag atccgacggc tggctatggt gcggcacaac caccgactac   600
gacaccgaca agctgtttgg ctactgtcct ctgaagtttg agggcagcga gagcctgtgg   660
aacaaggacc ccctgaccct ggtctcttat cagatcaaca gcaagtccgc cctgacctgg   720
caccaggcta gaaagtcctg ccaacagcag aatgccgagc tgctgtctat tacagagatc   780
cacgagcaga catacctgac tggcctgaca agcagcctga cgtcagggct gtggattgga   840
ctcaacagcc tgtcattcaa ctcaggctgg cagtggtctg atagaagccc gttccggtac   900
ctgaattggc tgcctggctc cccctctgcc gagcccggca agtcttcgtg gagtctgaac   960
cccggaaaga acgctaagtg ggaaaacctg gaatgcgtgc agaagctggg ctacatttgc  1020
aaaaagggca ataccacact gaactcattc gtgatcccta gcgagtctga cgtgcccaca  1080
cattgcccga gccagtggtg gccctacgcc ggccactgtt acaagatcca tagagatgag  1140
aagaagattc agagagatgc cctgaccaca tgcagaaagg aaggcggcga cctgacatct  1200
attcacacga ttgaggaact ggacttcatc atcagccagc tgggctatga acctaacgac  1260
gagctgtgga tcggtctgaa cgacatcaag atccagatgc actttgagtg gagcgatgga  1320
acacctgtga ccttcaccaa gtggctgagg ggcgaaccta gccacgagaa caatagacaa  1380
gaagattgcg tcgtgatgaa gggcaaagac ggctactgga cggatcgggg ctgcgagtgg  1440
cctctggggt acatctgcaa gatgaagagc agaagccagg gccccgaaat tgtggaagtg  1500
gaaaagggct gtagaaaggg ctggaaaaag caccacttct actgctacat gatcggccac  1560
actctgtcta ccttcgccga agctaaccag acctgcaaca acgagaacgc ctacctgaca  1620
accatcgagg atagatacga gcaggccttc ttacgagct ttgttggact gagacctgaa  1680
aagtacttct ggacgggcct gagcgacatc cagaccaagg gcacgttcca gtggacgatc  1740
gaagaggagg tgagattcac ccactggaac agcgatatgc ccggcagaaa gccaggctgc  1800
gtggccatga ggaccggaat cgccggaggc ctgtgggacg tgctgaagtg cgacgagaaa  1860
gccaagttcg tgtgcaagca ctgggccgag ggcgtgaccc atcctcctaa gcccacaact  1920
actccagaac ctaagtgccc cgaggattgg ggcgcctcta gcagaaccag cctgtgcttc  1980
aaactgtacg ccaagggcaa acacgagaag aagacctggt tcgagagcag agatttctgc  2040
agagccttag gcggagacct tgcttccatc aacaacaaag aggaacagca gaccatctgg  2100
agactgatca cggcctctgg ttcctatcac aagctctttt ggttgggcct gacctacggc  2160
tctcctagcg agggcttcac ctggagcgac ggatctcctg tgtcctacga gaattgggcc  2220
tacggcgagc ccaacaacta ccagaacgtg gaatactacg gcgagcttaa gggggaccct  2280
acgatgagct ggaatgacat caattgtgaa cacctgaaca actggatctg tcagatccag  2340
aagggacaaa ccctaagcc tgagcctaca cctgcccctc aggacaatcc tccagtgaca  2400
gaggacggct gggtcatcta caaggactac cagtactact tcagcaagga gaaagacca  2460
atggacaacg ccagagcctt ttgcaagcgg aatttcggcg acctggtcag catccaatcc  2520
gaatccgaga gaagttcct gtggaagtac gtgaatagaa acgacgccca gagcgcctat  2580
ttcatcggcc tcctgattag cctggataag aagttcgcct ggatggacgg cagcaaagtg  2640
gactacgtgt cctgggccac tggagagcct aacttcgcca acgaagatga aaactgcgtg  2700
accatgtaca gcaatagcgg attctggaac gatatcaact gcggctaccc caacgctttc  2760
atctgccaaa gacacaactc ttccatcaac gccacaaccg tgatgcctac catgcctagc  2820
gtgccatccg gctgtaaaga aggctggaac ttctactcga caagtgctt caagatcttc  2880
ggcttcatgg aagaagaacg gaagaactgg caggaggcca gaaaggcctg catcggtttc  2940
ggcggcaatc tggttagcat ccagaacgag aaagaacagg ccttcctaac ataccacatg  3000
aaggacagca ccttttctgc ctggacaggg ctgaacgatg tgaacagcga acacacattc  3060
ctctggactg atggtagagg cgtgcactac accaactggg gaaaaggcta ccctggcgga  3120
agacggtcta gcctgagtta cgaggatgcc gattgcgtgg ttatcattgg cggcgctagc  3180
aatgaggccg gcaagtggat ggacgacacc tgtgacagca agcgaggata tatctgtcag  3240
accagatccg atcctagcct gacaaatccg cccgccacga tccaaaccga cgggttcgtg  3300
```

-continued

```
aagtacggca agagctctta cagcctgatg agacagaagt tccagtggca cgaggccgaa    3360
acctactgca agctgcacaa cagcctcatc gcctccatcc tggaccctta cagcaacgcc    3420
tttgcttggc tgcagatgga aaccagcaac gagagagtgt ggattgccct gaattcaaac    3480
ctcacagata accagtacac atggacagat aagtggcggg tgcggtacac caactgggct    3540
gcagatgagc ccaaactgaa gtctgcctgt gtgtacctgg acctggacgg ctactggaag    3600
accgcccact gtaatgagtc cttttacttc ctgtgcaagc ggagcgacga aatcccagcc    3660
accgagcctc cacagctgcc cggcagatgc cccgaaagcg accacaccgc ctggatcccc    3720
ttccacggcc actgttacta catcgagtct tcctacacaa gaaactgggg ccaggcctca    3780
ctggaatgtc tgagaatggg cagcagcctg gtgtcaatcg agtcagccgc cgagtcctcc    3840
ttcctgagct acagagtgga acctctgaag agcaagacaa acttctggat cggccttttt    3900
agaaacgtgg aaggaacctg gctgtggatc aacaactccc ctgtgagctt cgtgaactgg    3960
aacaccggcg acccctctgg cgagcggaac gattgcgtgg ccctgcacgc cagcagcgga    4020
ttttggtcca acatccactg ctcttcctat aagggctata tctgtaaaag acccaaaatc    4080
atcgacgcca agcccaccca cgaactgctg acaacaaagg ccgacacccg gaagatggat    4140
cctagcaagc cctcttccaa cgtggccggc gtggtcatca tcgtgatcct gctgatcctg    4200
acaggcgccg gcctggccgc ttactttttc tacaagaaaa gaagggttca tctgcctcag    4260
gagggcgcct tcgagaacac cctctacttt aactctcaga gcagccctgg aacatcagac    4320
atgaaagacc tggtgggcaa catcgagcag aacgagcact ctgtgatctg a             4371
```

NEOEPITOPE VACCINE DELIVERY VEHICLE AND METHODS OF MAKING THE SAME

CROSS-REFERENCE TO RELATED APPLICATIONS

This application claims the benefit of priority under 35 U.S.C. § 119 (e) to U.S. Provisional Patent Application No. 63/287,176, filed Dec. 8, 2021. The entire disclosure of U.S. Provisional Patent Application No. 63/287,176 is incorporated herein by reference.

REFERENCE TO A SEQUENCE LISTING

This application contains a Sequence Listing submitted electronically as an ST.26 XML file. The xml file, named "PAT005304_Sequence_Listing.xml", has a size of 6339 bytes, and was recorded on 6 Dec. 2022. The information contained in the xml file is incorporated herein by reference in its entirety.

BACKGROUND

Significant effort has been invested in the design of colloidal drug carriers in order to improve drug localization and bioavailability. Ideally, an actively targeted particulate drug carrier will increase the therapeutic efficacy of a drug by delivery to the diseased site, while reducing drug-associated side effects. Attainment of this goal would greatly advance treatment of diseases (e.g., cancer) where the toxic effects of therapeutics administered systemically may outweigh their benefit. To date, many types of delivery vehicles have been explored for in vitro and in vivo drug delivery applications, including inorganic nanoparticles, polyelectrolyte complexes, liposomes, block co-polymer micelles, and polymeric nanoparticles.

Several nanoparticle vaccine delivery platforms are under development wherein the fastest prime dose delivery as possible is being sought. A synthetic nano-scale vehicle offers a number of advantages such as bottom-up functional design, protection in vivo for sensitive bioactive cargo such as peptides and allows for scalable and reproducible production.

Disclosed herein is a novel nanogel vaccine platform that is made by induced self-assembly of the polysaccharide mannan. The gel nanoparticles are decorated with mannan chains (to draw the particles to the CD206 receptor) and cleavable neoepitope peptides. These nanoparticles can be manufactured quickly according to the methods disclosed herein.

SUMMARY

Disclosed herein is a method of making a self-assembling mannan nanogel for in vivo delivery of therapeutic agents, the method comprising: oxidizing mannan with periodate (NaIO4); purifying the oxidized mannan; adding aniline to the purified oxidized mannan to produce a mannan derivative with hydrophobic phenylimine groups covalently attached to the mannan; and sonicating the mannan derivative.

In one aspect, dihydrazide (DH) crosslinkers are introduced into the self-assembled mannan nanogel, the method comprising reacting the mannan nanogel with succinate dihydrazide (SDH) and 3,3'-Dithiobis(propanoic dihydrazide) (DPDH).

In one aspect, the dihydrazide crosslinked mannan nanogels are prepared for loading with a thiol-containing cargo, the method comprising reducing nanogel disulfide crosslinks with (tris(2-carboxyethyl) phosphine) (TCEP), reducing nanogel imines and residual aldehydes with borohydride (NaBH4), and activating nanogel thiols with 2,2-dithiopyridine (DTP).

In still another aspect, the thiol-containing cargo is loaded onto the DTP-activated nanogel, wherein the cargo is comprised of one or more peptides, and optionally glutathione (GSH).

In yet another aspect, dihydrazide crosslinked nanogels are coated with NaIO4-oxidized mannan.

In one aspect, diamine (DA) crosslinkers are introduced into the mannan nanogel, the method comprising sequentially reacting the mannan nanogel with cystamine and ethylenediamine dihydrochloride (EDA), and then Sodium cyanoborohydride (NaCNBH$_3$).

In one aspect, the diamine crosslinked mannan nanogels are prepared for loading with a thiol-containing cargo, the method comprising reducing nanogel disulfide crosslinks with (tris(2-carboxyethyl) phosphine) (TCEP), and activating nanogel thiols with 2,2-dithiopyridine (DTP).

In one aspect, the thiol-containing cargo is loaded onto the DTP-activated nannogel, wherein the cargo is comprised of one or more peptides, and optionally glutathione (GSH).

In one aspect, diamine crosslinked nanogels are coated with NaIO4-oxidized mannan and then reacted with Sodium cyanoborohydride (NaCNBH$_3$).

Also disclosed herein is a method of loading thiol-modified RNA onto DTP-activated dihydrazide crosslinked or diamine crosslinked mannan nanogels, the method comprising 1) reductive amination of oxidized RNA, wherein oxidized RNA is sequentially reacted with cystamine and TCEP, 2) purification, and 3) addition to DTP-activated nanogels.

Also disclosed herein is a method of loading RNA onto the DTP-activated diamine crosslinked mannan nanogels, the method comprising adding unmodified RNA to the DTP-activated nanogels.

Also disclosed herein is a composition comprising CD206-expressing 293T cells, wherein the 293T cells are genetically engineered to stably express a gene having the sequence of SEQ ID NO: 1.

Further disclosed herein is a method of quantifying cellular uptake of mannan nanogels or cargo loaded mannan nanogels, the method comprising treating CD206-expressing 293T cells with a mannan nanogel, wherein the 293T cells are genetically engineered to stably express a gene having the sequence of SEQ ID NO: 1, and wherein cellular uptake of the nanogel or cellular expression of the cargo is quantified.

In one aspect of the method of quantifying cellular uptake, quantification is by fluorescence, luminescence, viability, apoptosis, cell size, cellular proliferation, spheroid formation, cell surface expression, or subcellular localization.

In one aspect of the method of quantifying cellular uptake, the mannan nanogel is doped with fluorescently labeled dextran. In one aspect, the fluorescent label is Fluorescein isothiocyanate (FITC)

DESCRIPTION OF THE DRAWINGS

FIG. 4A shows a schematic for how peptide cargo can be loaded onto nanogels via disulfide formation.

FIG. 4B shows the structure of FITC-RP426C.

FIG. 4C shows the structure of TCEP.

FIGS. 6A-6C show nanogel antigen delivery and presentation established using ELISPOT. FIG. 6A is a schematic representation. FIG. 6B shows results for NLV-mod peptide and FIG. 6C shows the results for DiHy and DiAm.

FIG. 9A shows the results with Hi-Ox mannan; FIG. 9B shows the results for Low-Ox mannan; and FIG. 9C shows the fold change between the two.

FIG. 11A shows the result after one hour. FIG. 11B shows a time course over 20 hrs.

FIG. 12A shows the oxidation level vs the percent positive for 293T-Neg and 293T-CD206.

FIG. 12B shows the oxidation level vs. the score fold change.

FIGS. 14A-14D show uptake and ELISPOT with GSH mixed cargo. FIG. 14A shows the results at 1:0; FIG. 14B shows the results at 1:1 and FIG. 14C shows the results at 1:9. FIG. 14D shows the interferon-gamma (INF-g) ELISPOT, NLP03.

FIG. 16A shows the 3'end of mRNA can be selectively thiolated by periodate oxidation followed by reductive amination with cysteine. FIG. 16B shows cationic (DA also referred to as DiAm) nanogels may also complex with mRNA by electrostatics along.

FIG. 17A show the gel uptake. FIG. 17B show the mCherry expression.

FIGS. 18A-18B shows the comparison of DiHY (FIG. 18A) and DiAM (FIG. 18B) mCherry RNA gels.

FIG. 19 shows the structure of mannan from *S. cerevisiae*.

DETAILED DESCRIPTION

Figure 1:
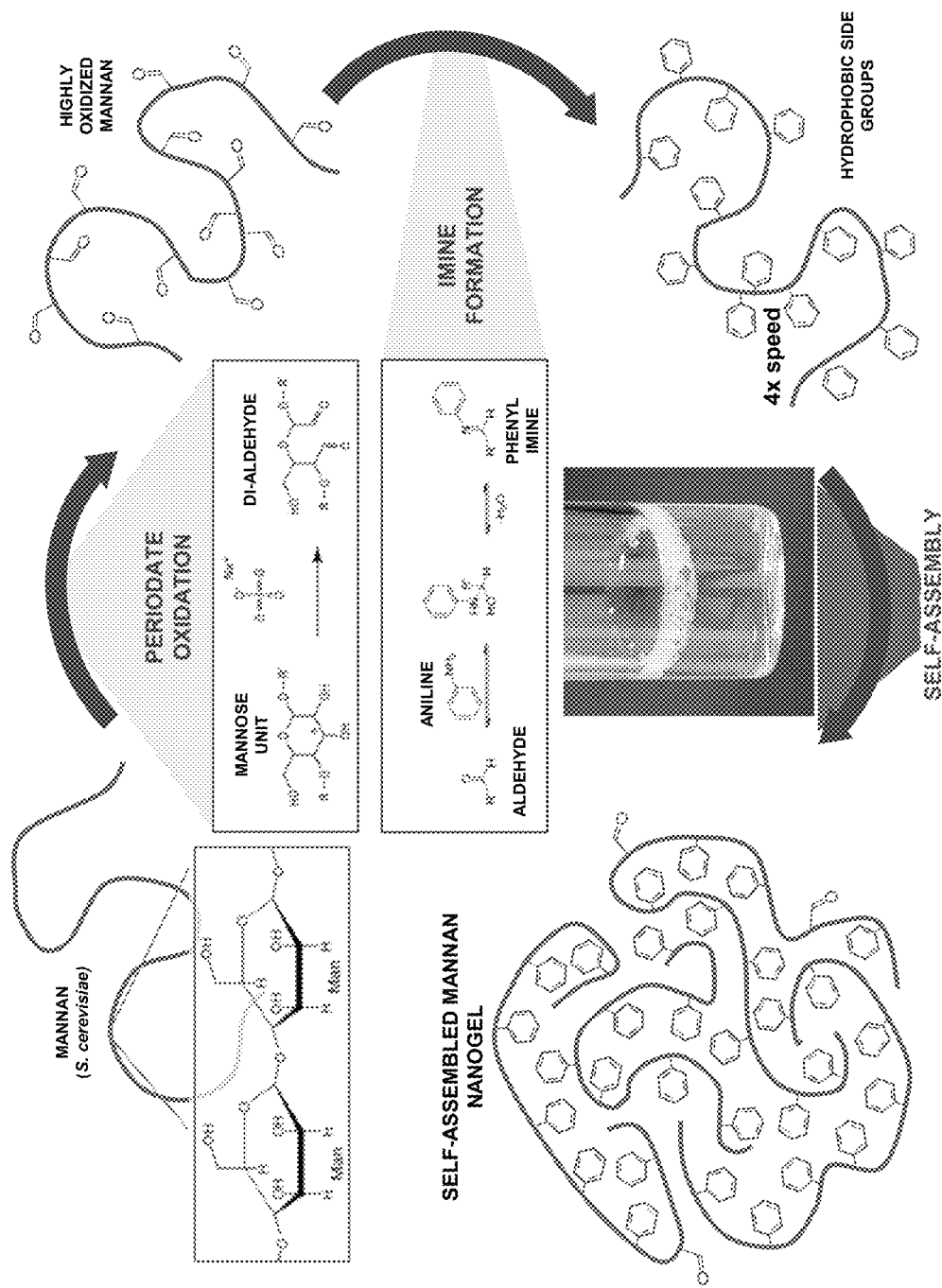
FIG. 1 shows a schematic of the novel self-assembly process of uniform mannan nanogels.
Figure 2B:
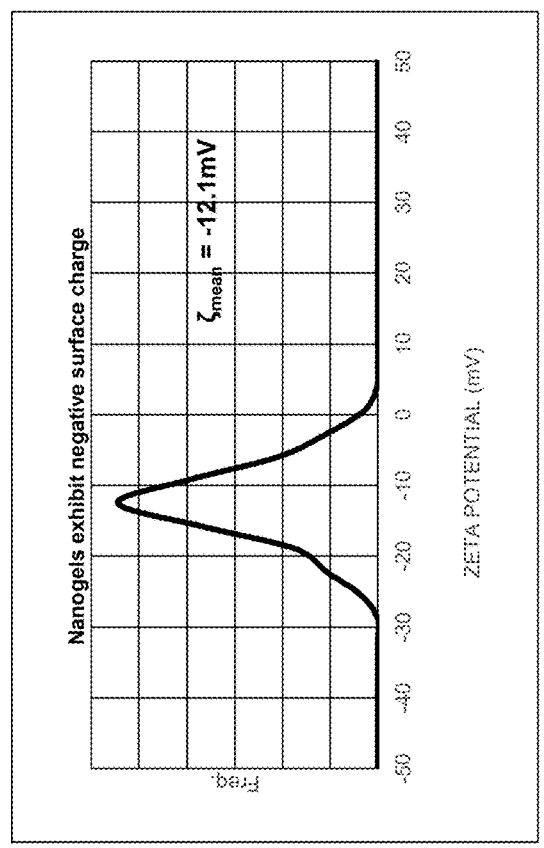
FIG. 2B shows that the nanogel exhibits negative surface charge.
Figure 2A:
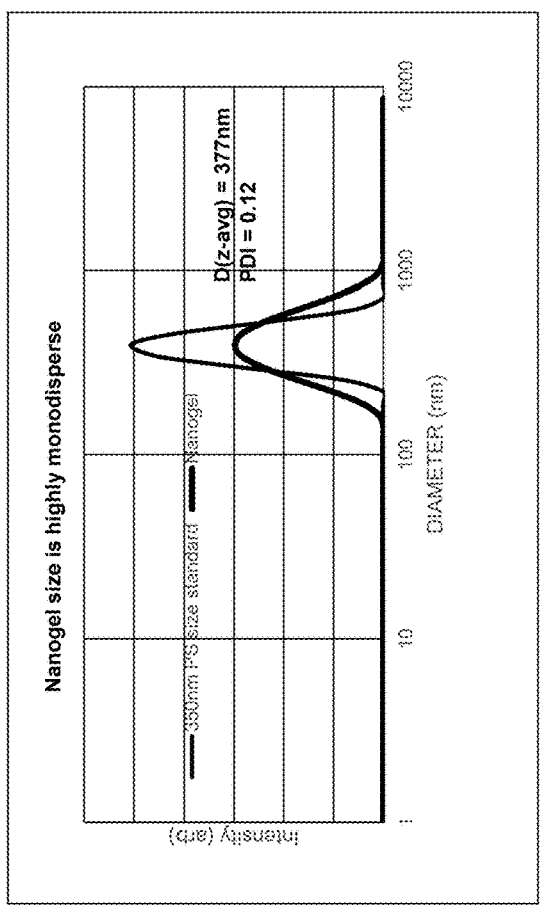
FIG. 2A shows that the nanogel size is highly monodispersed.
Figure 2C:
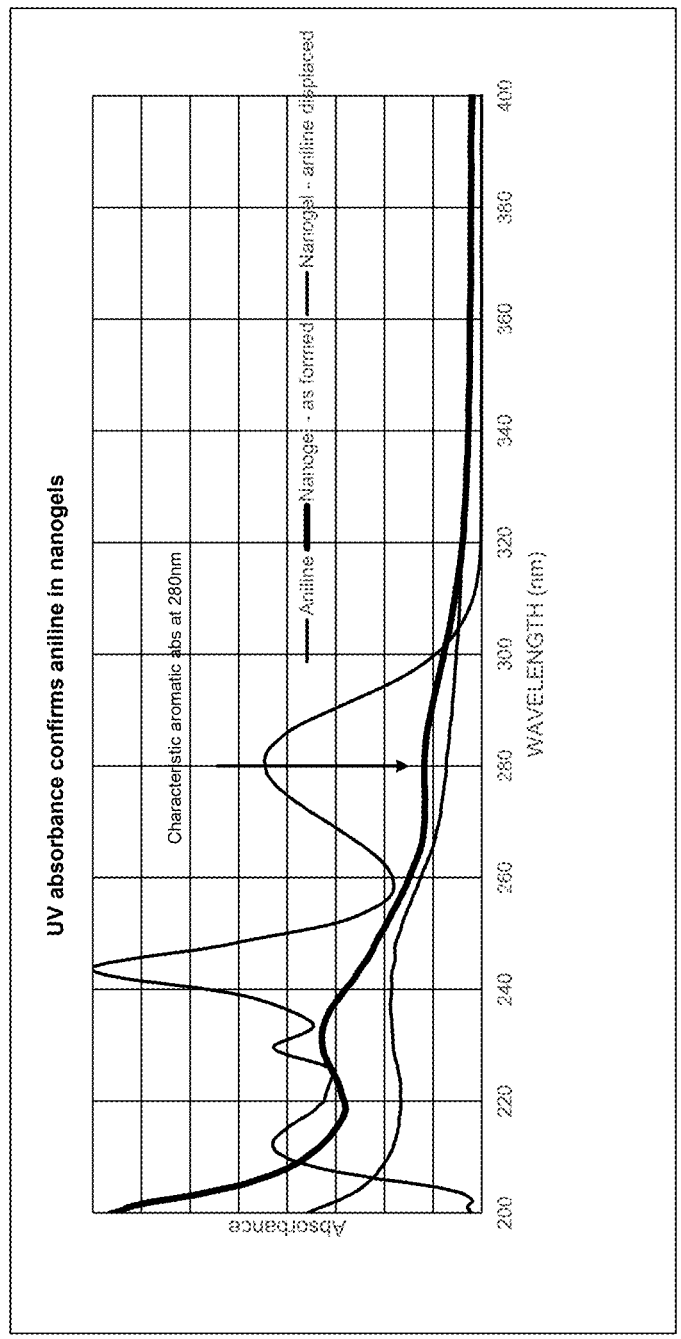
FIG. 2C show that the ultra-violet (UV) absorbance confirms aniline in nanogels.
Figure 3:
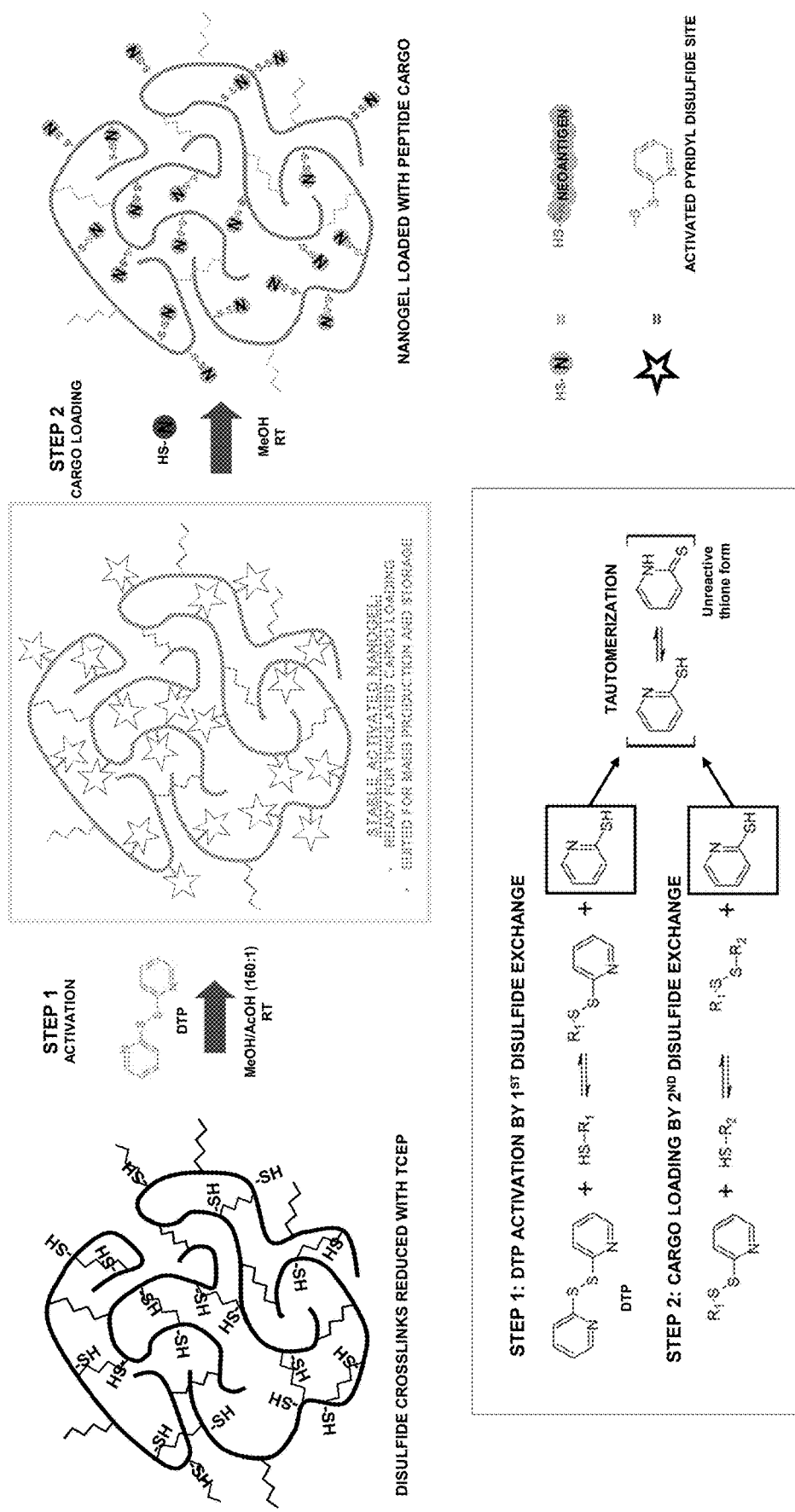
FIG. 3 shows a schematic of the steps when the nanogels are activated with DTP and peptide cargo is loaded.
Figure 4D:
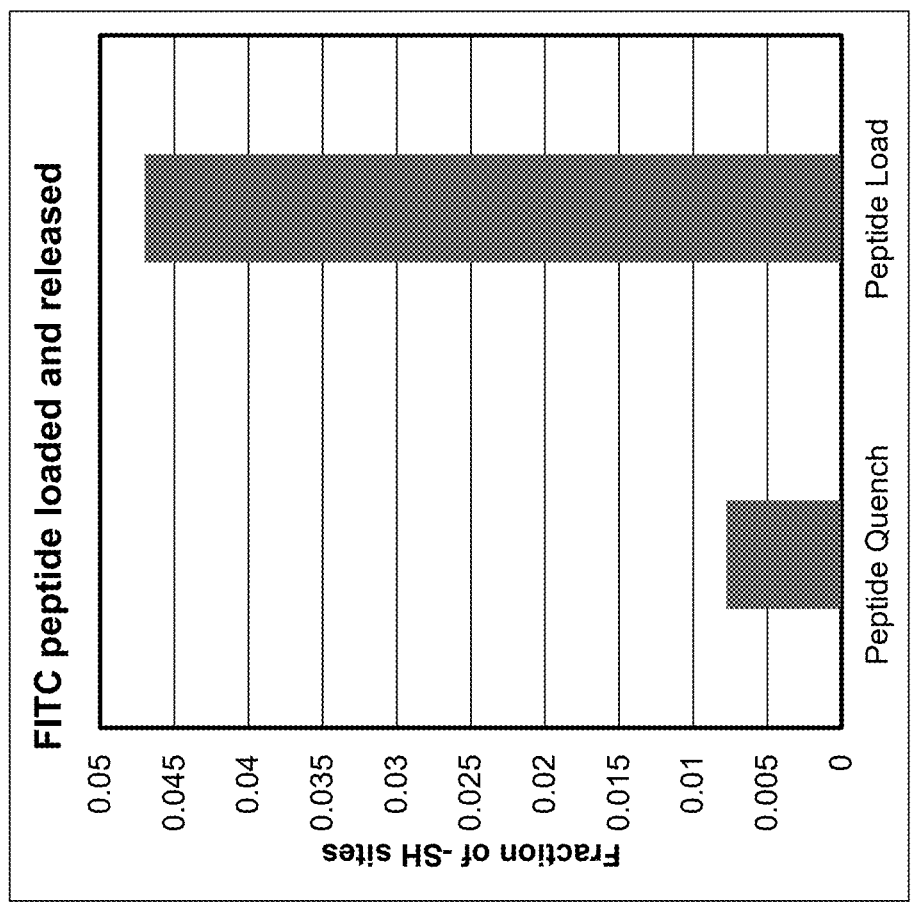
FIG. 4D shows the fraction of thiol (—SH) thiol sites with FITC peptide loaded and released.
Figure 5:
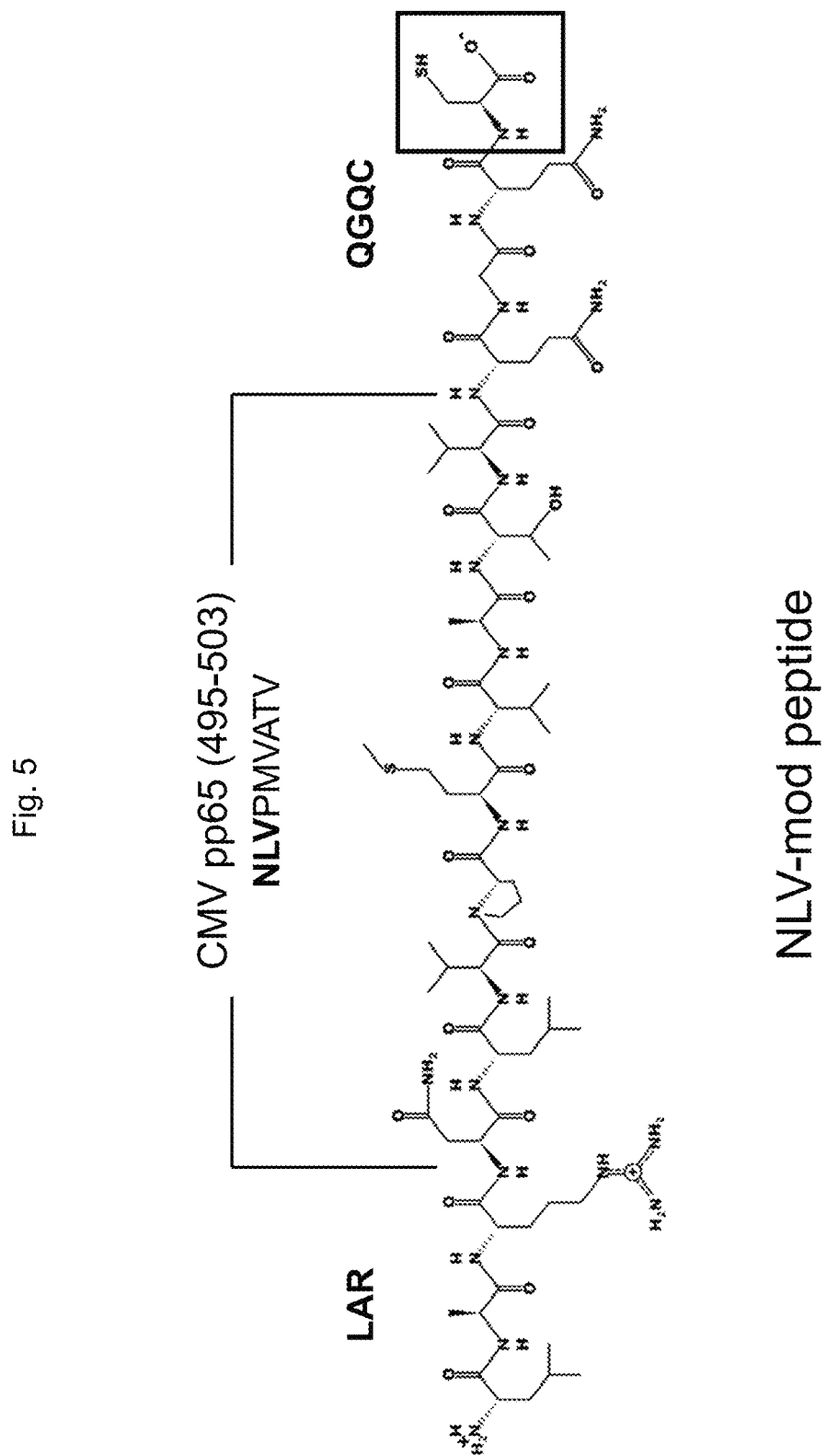
FIG. 5 shows a modified cytomegalovirus (CMV) antigen peptide for disulfide attachment. The box at the end of structure shows the "C" of QGQC.
Figure 7A:
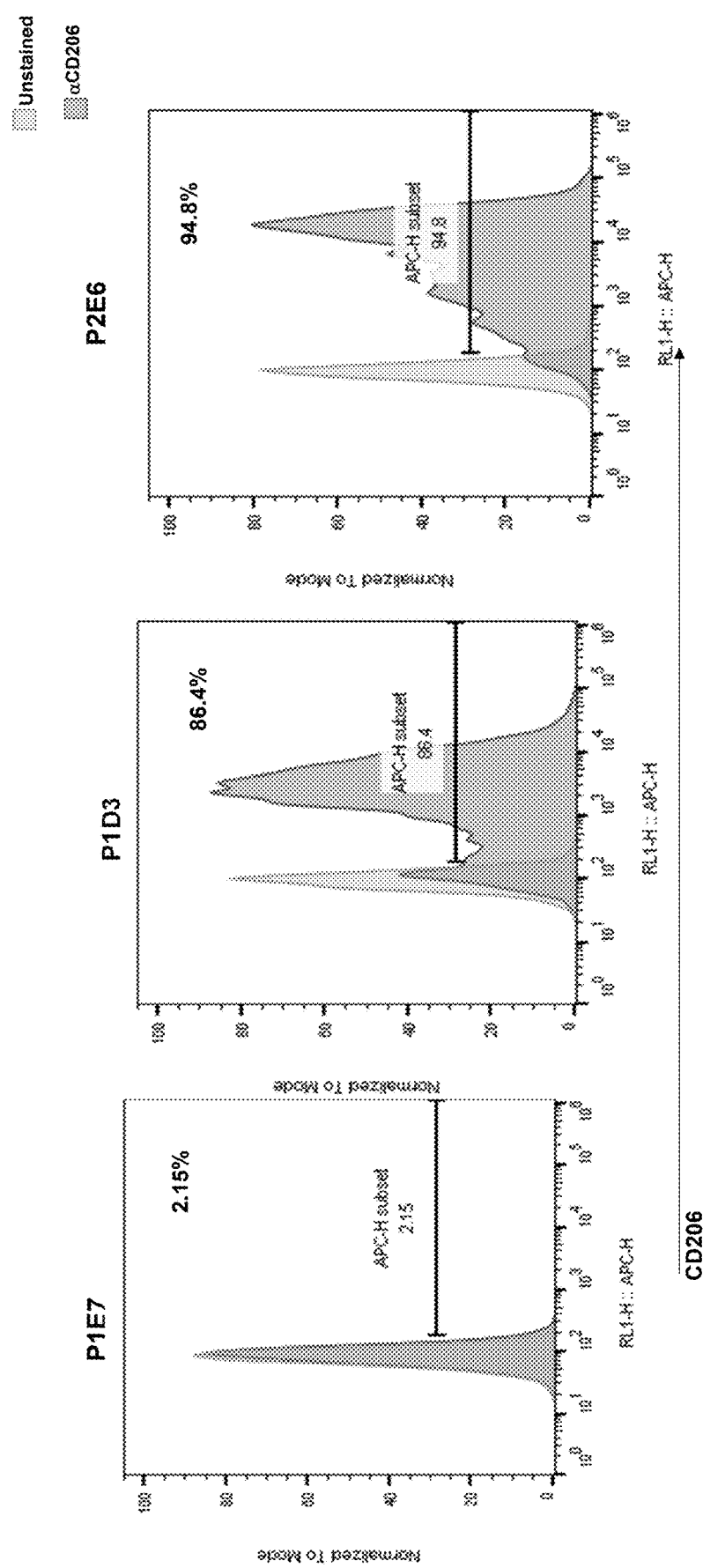
FIGS. 7A and 7B show stable 293T cell lines developed to express CD206.
Figure 7B:
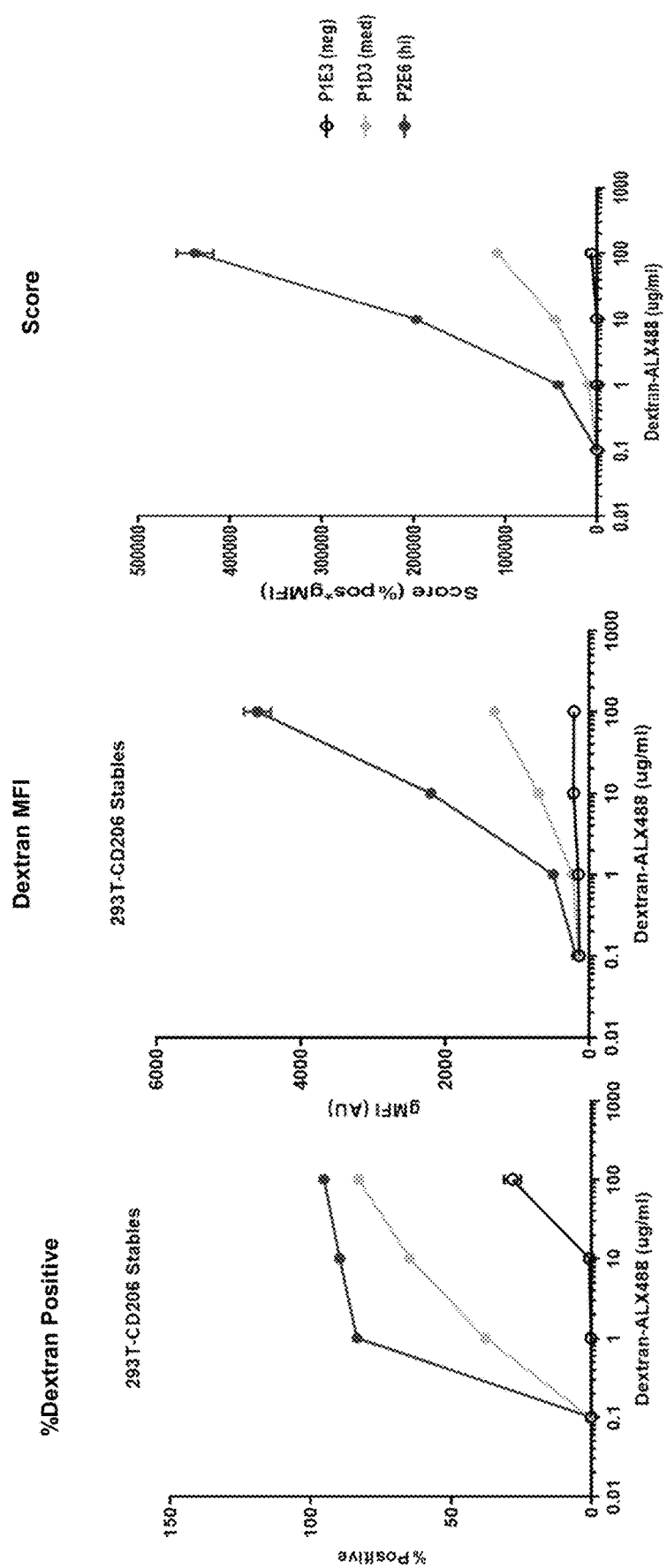
Figure 8:
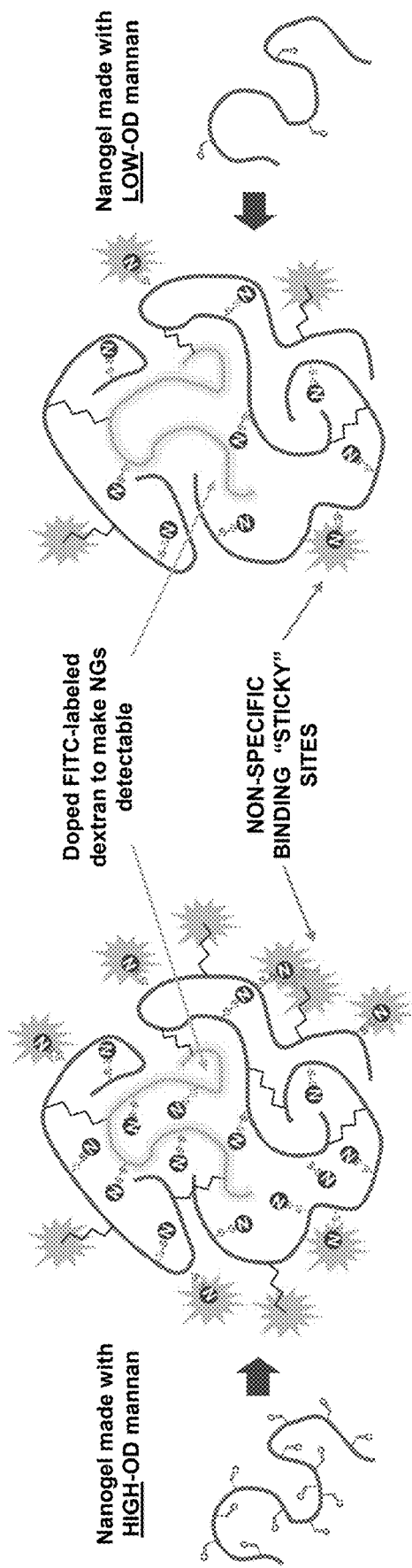
FIG. 8 shows a schematic of nanogels made with either high or low oxidation mannan.
Figure 9C:
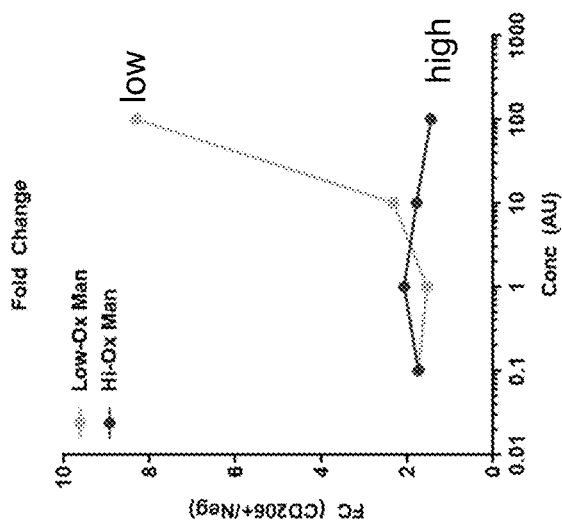
FIGS. 9A-9C show low-oxidation mannan results in differential nanogel uptake by cell lines. The degrees of oxidation (OD or OX) of mannan determines the prevalence of reactive aldehydes. Fewer aldehydes result in fewer downstream surface groups susceptible to non-specific binding (e.g., charged, highly poler or hydrophobic). Differential uptake of low-OD mannan gels by CD206-bearing cells could indicate improved receptor affinity, reduced non-specific binding or a combination. Low-OD mannan also produces less stable gels with lower cargo carrying capacity.
Figure 9B:
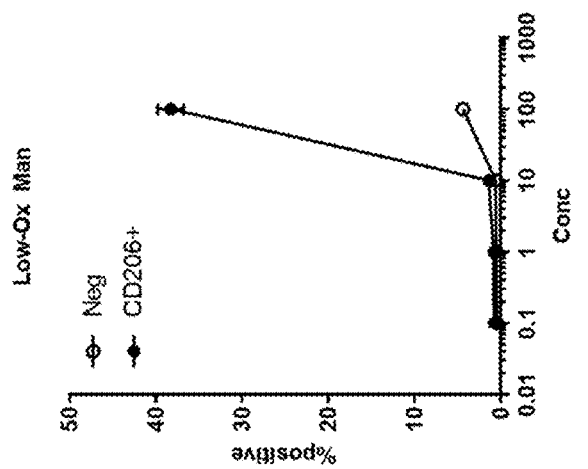
Figure 9A:
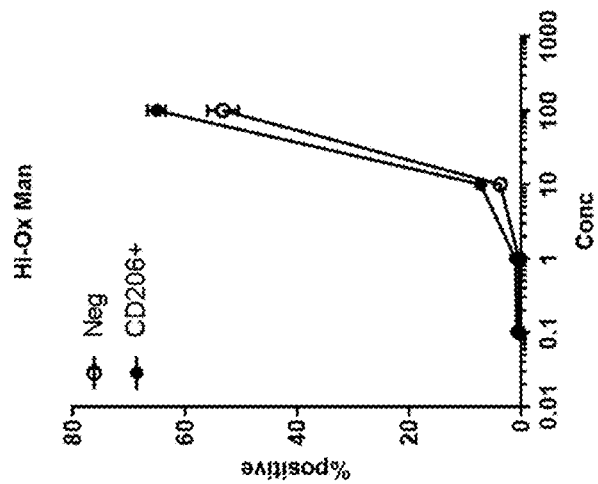
Figure 10:
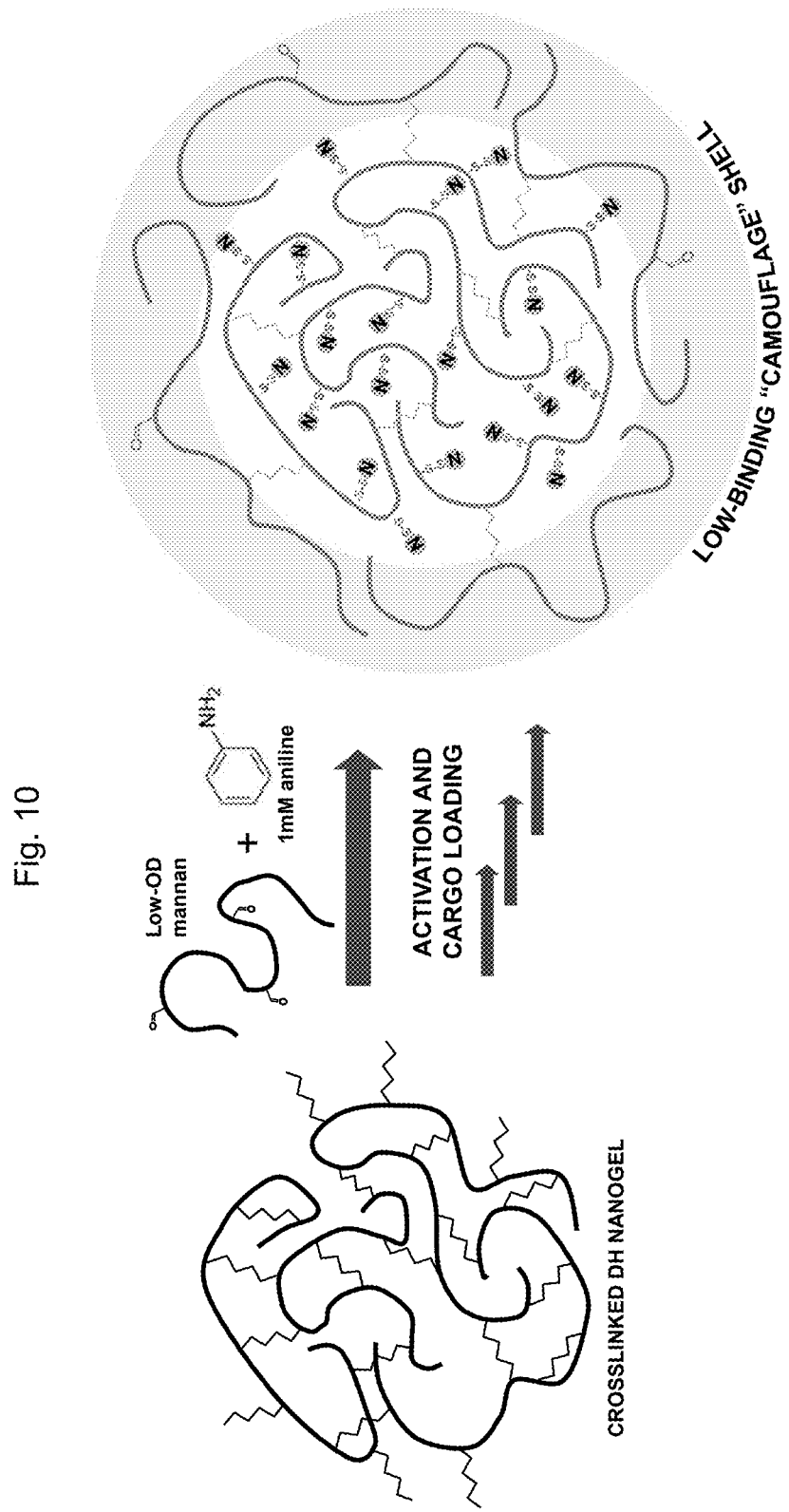
FIG. 10 shows a schematic of secondary mannan assembly. Dangling crosslinkers remain reactive to aldehydes. Low-OD mannan retains enough aldehydes to react with the core-gel, but few other sites for non-specific binding. A secondary core-shell assembly using low-OD mannan should impart a 1ow-binding surface.
Figure 11B:
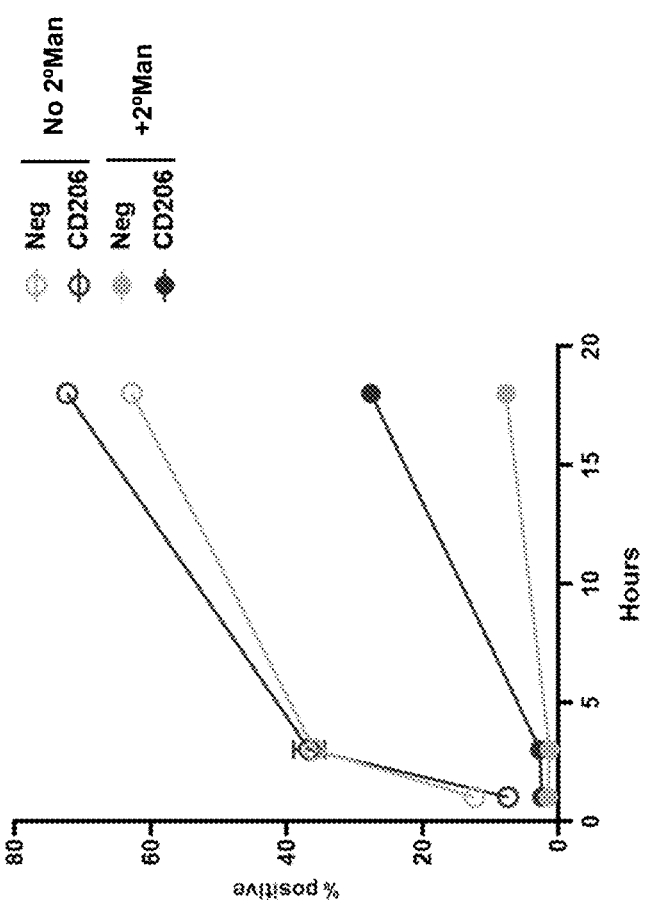
FIGS. 11A and 11B show secondary mannan reduces non-specific uptake and imparts CD206 specificity.
Figure 11A:
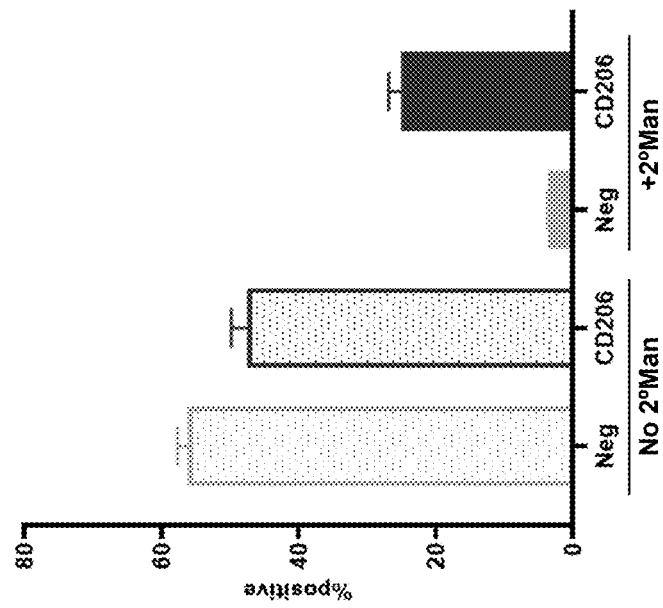
Figure 12A:
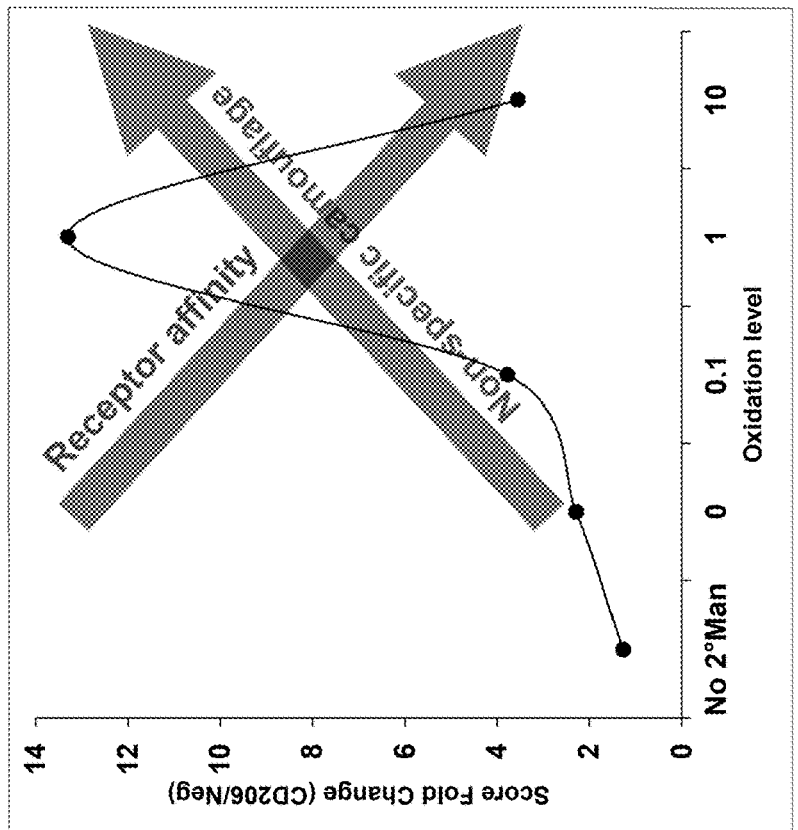
FIGS. 12A and 12B shows oxidation level of secondary mannan optimized for CD206 specific uptake.
Figure 12B:
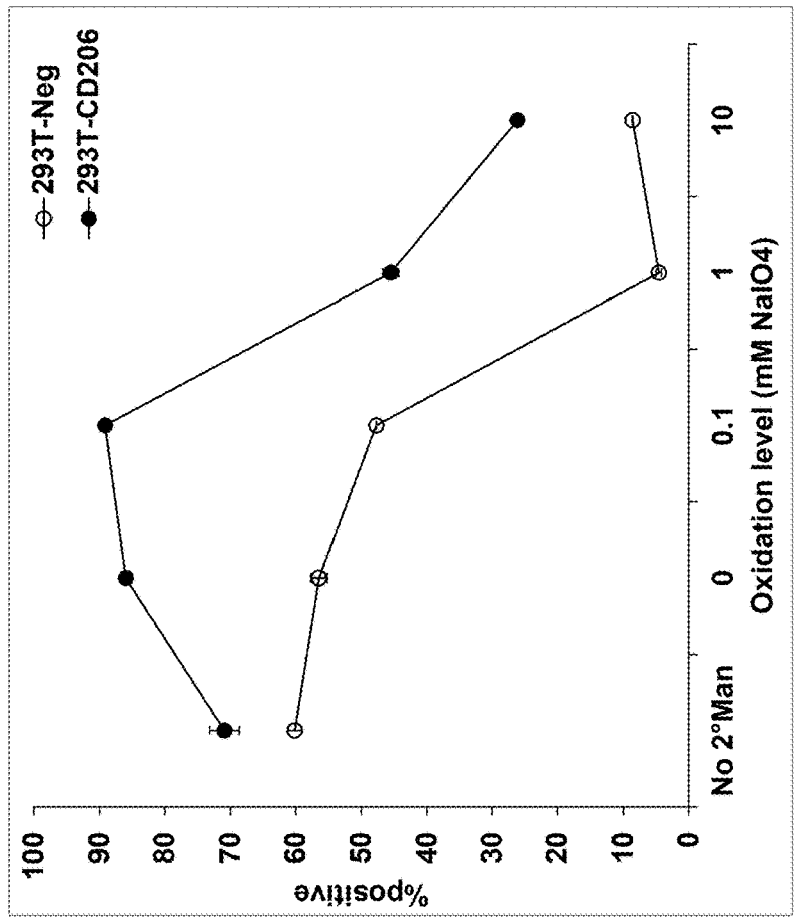
Figure 13C:
FIG. 13C shows the structure of glutathione (GSH).
Figure 13B:
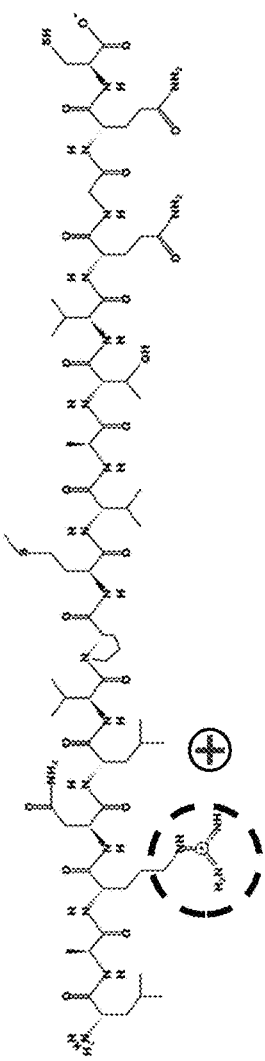
FIG. 13B shows the structure of the NLV-mod antigen peptide.
Figure 13A:
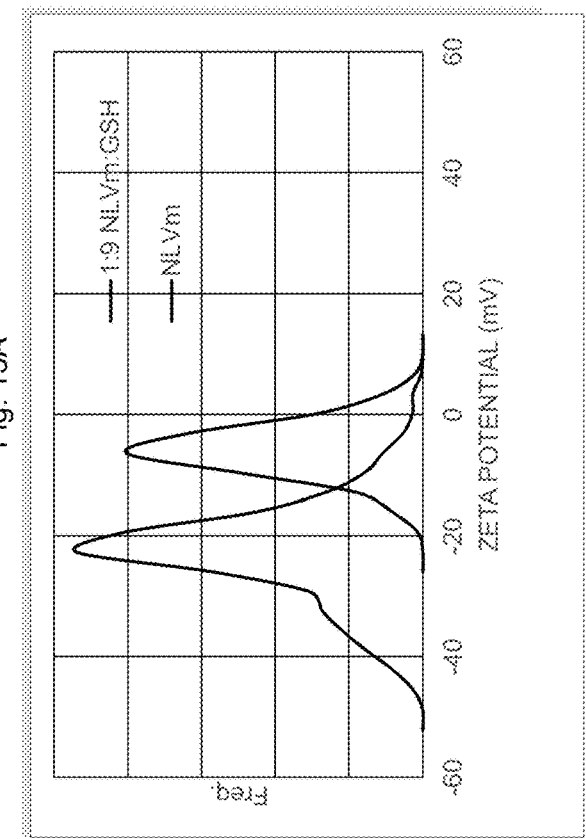
FIG. 13A shows nanogel surface charge can be controlled by cargo mixture. NLV-mod carries a net+charge. GSH carries a net-1 charge. Nanogels were loaded with peptides mixed at different ratios (NLV-mod:GSH). Observed zeta potentials reflect expected surface charge changes. The NVL peptide is an HLA-A2 restricted peptide from cytomegalovirus (CMV). It is used as a control peptide for CD8 T-cell stimulation.
Figure 15A:
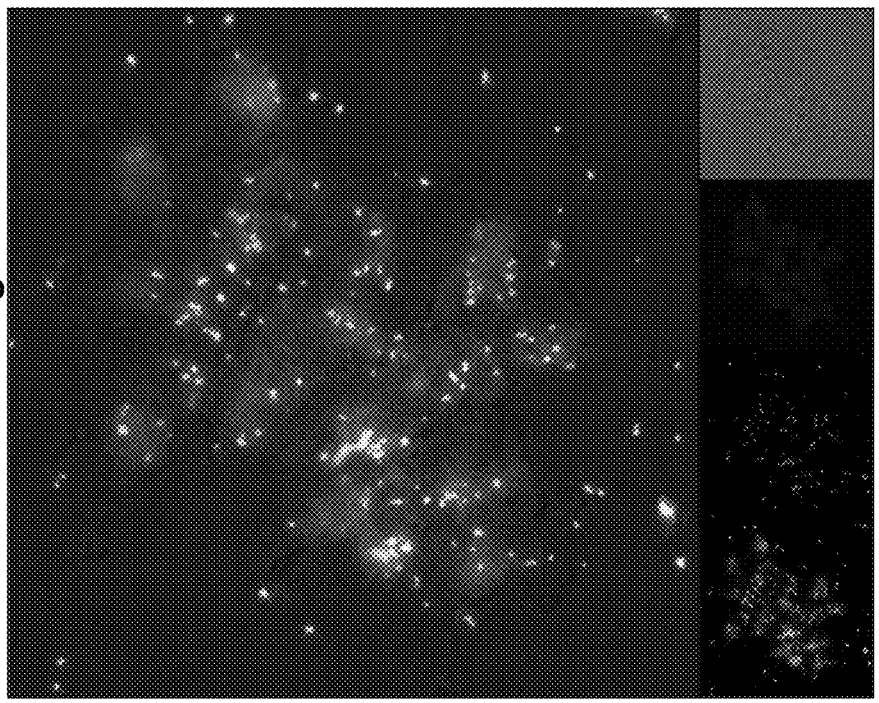
FIGS. 15A-15B show intracellular co-localization of nanogel and peptide in CD206 positive 293T cells at 1 hour (FIG. 15A) and overnight (FIG. 15B).
Figure 15B:
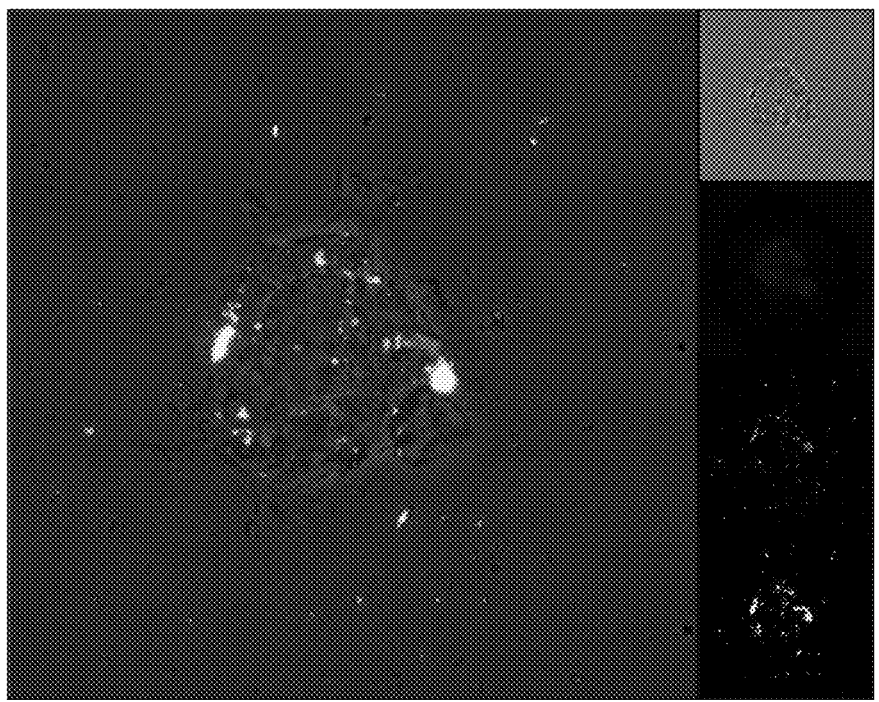
Figure 16A:
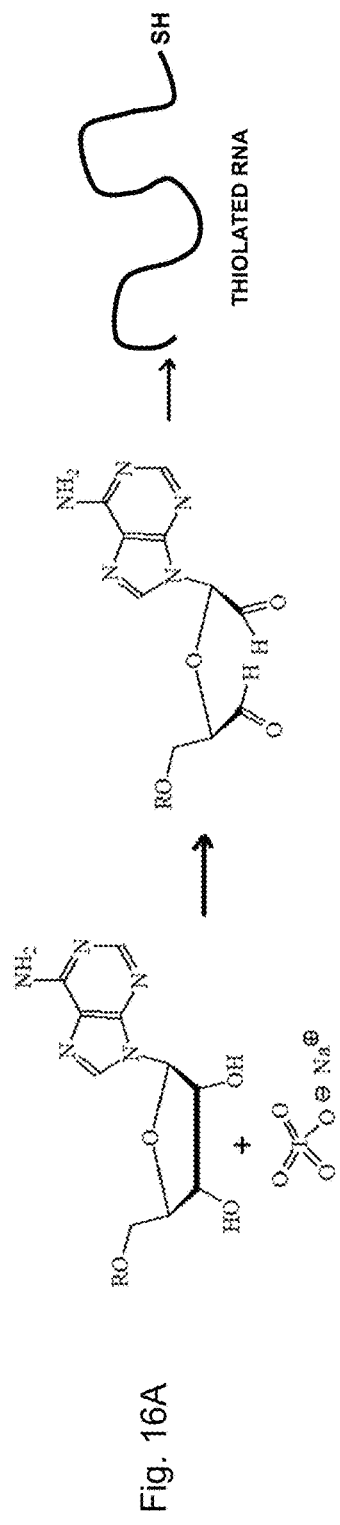
FIGS. 16A-16B show schematics of RNA as nanogel cargo.
Figure 16B:
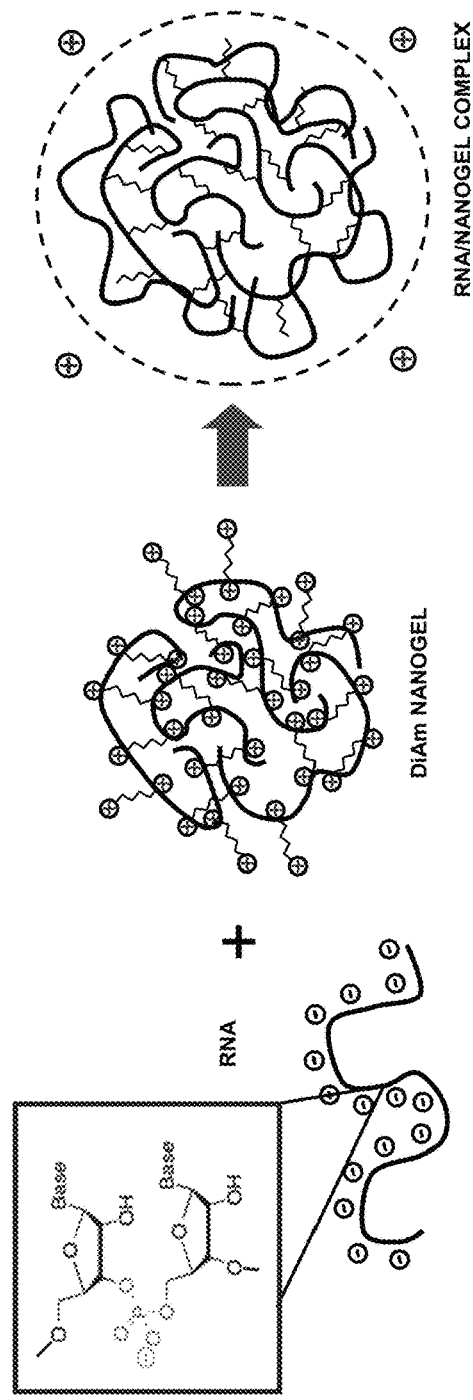
Figure 17B:
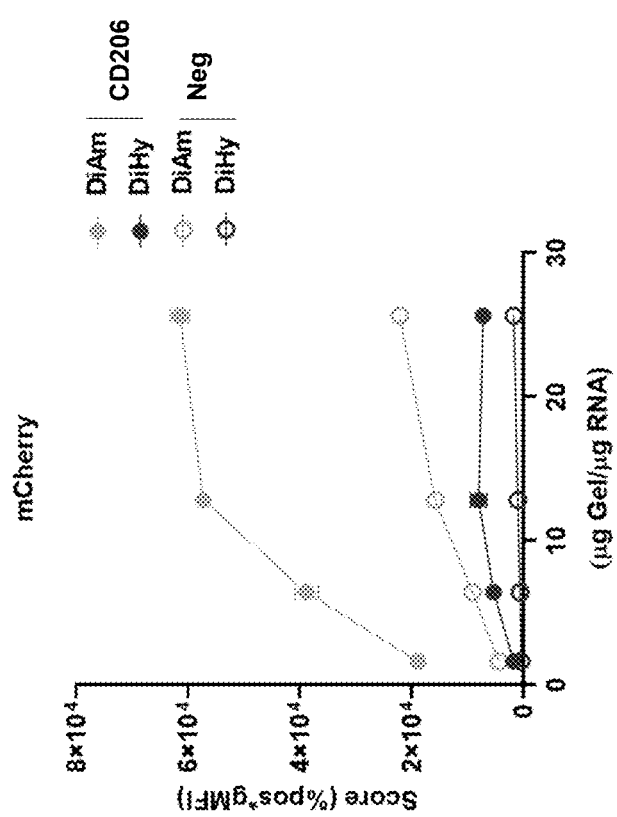
FIGS. 17A-17B show that DiAm and DiHy nanogels deliver mCherry mRNA.
Figure 17A:
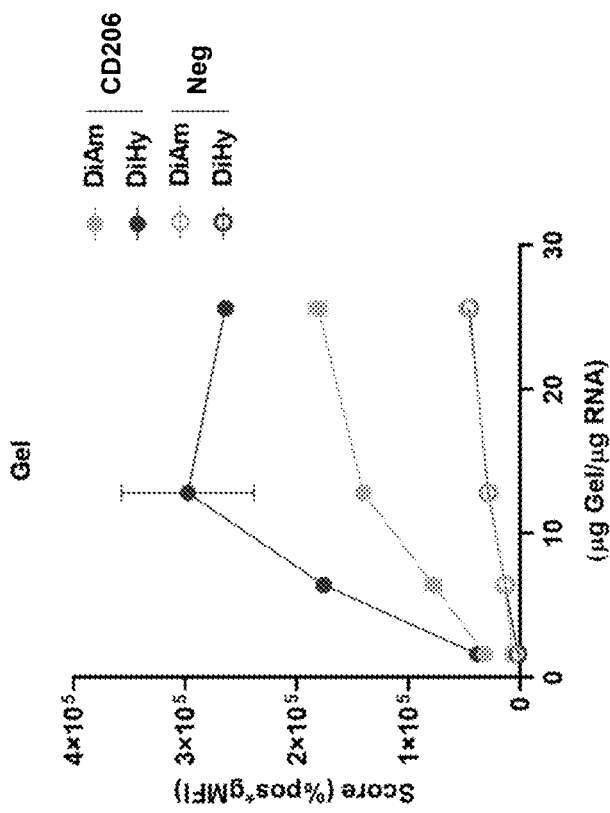

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry are those well-known and commonly used in the art.

All publications, patents, and published patent applications referred to in this application are specifically incorporated by reference herein. In case of conflict, the present specification, including its specific definitions, will control.

Mannan nanogels as a novel vaccine delivery platform as well a novel method of making a self-assembling mannan nanogel for in vivo delivery of therapeutic agents are disclosed herein. Mannan targets dendritic cells (DCs) through C-type lectins. The mannose receptor (CD206) is highly expressed on DC cell surfaces. The targeting of mannan nanogels to DCs has been validated by the inventors using a stable CD206 expressing cell line. Therapeutic agents, including but not limited to peptides, can be linked by disulfides via cysteines. The method comprises oxidizing mannan with periodate (NaIO4); purifying the oxidized mannan; adding aniline to the purified oxidized mannan to produce a mannan derivative with hydrophobic phenylimine groups covalently attached to the mannan; and sonicating the mannan derivative.

The expression of CD206 is limited in humans to DCs, macrophages and in subpopulation of endothelial cells. CD206 activation mediates endocytosis, which is ideal for processing of antigen cargo. Therefore, peptides bound to mannan nanogels are targeted to CD206-expressing dendritic cells, whereby the peptides are internalized, processed, and presented by the dendritic cells to activate T cells specific for the bound peptide.

In one aspect, crosslinkers are introduced into the self-assembled mannan nanogel. Crosslinking turns hydrophobic assemblies into covalent networks. As disclosed herein, crosslinkers can be diamines or dihydrazides, they can displace aniline by transamination, provide stable interchain bonds and introduce disulfide linking sites. Dihydrazide (DH) crosslinkers require organic solvents, reduce imines to hydrazides, and these DH crosslinkers introduce no charge to the network at physiological pH. Diamine (DA) crosslinkers are water soluble, reduce imines to secondary amines, and these DA crosslinkers introduce a cationic (+) charge to the network.

In one aspect, DH crosslinkers are introduced into the self-assembled mannan nanogel, the method comprising reacting the mannan nanogel with succinate dihydrazide (SDH) and 3,3'-Dithiobis(propanoic dihydrazide) (DPDH).

As disclosed herein the DH crosslinked mannan nanogels can be prepared for loading with a thiol-containing cargo. The method of loading comprises reducing nanogel disulfide crosslinks with (tris(2-carboxyethyl) phosphine) (TCEP), reducing nanogel imines and residual aldehydes with borohydride (NaBH4), and activating nanogel thiols with 2,2-dithiopyridine (DTP). The thiol-containing cargo is then loaded onto the DTP-activated nanogel. The cargo comprises one or more peptides and optionally glutathione (GSH). In one aspect, the DH crosslinked nanogels can be further coated with NaIO4-oxidized mannan.

Also disclosed herein are DA crosslinkers that can be introduced into the mannan nanogel. The method comprises sequentially reacting the mannan nanogel with cystamine and ethylenediamine dihydrochloride (EDA), and then Sodium cyanoborohydride (NaCNBH$_3$). In one aspect, the DA crosslinked mannan nanogels are prepared for loading with a thiol-containing cargo, the method comprising reducing nanogel disulfide crosslinks with TCEP, and activating nanogel thiols with DTP. The thiol-containing cargo is then loaded onto the DTP-activated nanogel, wherein the cargo is comprised of one or more peptides, and optionally GSH. In one aspect, DA crosslinked nanogels are coated with NaIO4-oxidized mannan and then reacted with Sodium cyanoborohydride (NaCNBH$_3$).

A further embodiment disclosed herein, is a method of loading thiol-modified RNA onto DTP-activated, DH crosslinked or DA crosslinked, mannan nanogels. This method comprises reductive amination of oxidized RNA, wherein oxidized RNA is sequentially reacted with cystamine and TCEP, followed by purification, and addition to DTP-activated nanogels.

Also contemplated is a method of loading RNA onto the DTP-activated DA crosslinked mannan nanogels, the method comprising adding unmodified RNA to the DTP-activated nanogels.

A further embodiment disclosed herein, is a method of quantifying cellular uptake of mannan nanogels or cargo loaded mannan nanogels. The method comprises treating CD206-expressing 293T cells with a mannan nanogel, wherein the 293T cells are genetically engineered to stably express a gene having the sequence of SEQ ID NO: 1, and wherein cellular uptake of the nanogel or cellular expression of the cargo is quantified. Quantification of the cellular uptake can be by fluorescence, luminescence, viability, apoptosis, cell size, cellular proliferation, spheroid formation, cell surface expression, or subcellular localization. In one aspect, the mannan nanogel is doped with fluorescently labeled dextran. In one aspect, the fluorescent label is FITC.

A further embodiment is a composition comprising CD206-expressing 293T cells. The 293T can be genetically engineered to stably express a gene having the sequence of SEQ ID NO:1.

As disclosed herein, nanogels are nanoparticles composed of a hydrogel that is highly cross-linked physically or chemically with hydrophilic polymer chains. Nanogels can hold a great amount of water due to the presence of hydrophilic functional groups. They are able to swell in good solvents while maintaining their internal structures. The term "nanogel" may refer to a crosslinked polymer particle capable of absorbing a fluid and retaining at least a portion of the fluid to form a swollen crosslinked polymer particle. A nanogel can have many sizes, and these sizes are indicative of the nanogel in solvent swollen form. Nanogel size may be optimized to remain in the bloodstream, and yet be capable of traversing fenestrated tumor vasculature.

A nanogel-based delivery system comprises an active agent or cargo contained substantially within the nanogel, wherein the active agent is covalently or non-covalently associated with the nanogel. As used herein, the term "active agent" or "cargo" can refer to one or more active agents or components, such as pharmacological component, a therapeutic component, a diagnostic component, a drug component, a biological component or the like. Thus, the terms "active agent," "cargo", "drug," "therapeutic," "diagnostic," "pharmaceutical," and the like may be used interchangeably throughout this disclosure. An active agent may also comprise one or more pharmaceutical additives including, but not limited to, solubilizers, emulsifiers, buffers, preservatives, carriers, suspending agents, thickening agents, stabilizers, inert components, and the like.

As used herein, the term "active agent" can include, without limitation, a biological or chemical compound such as a simple or complex organic or inorganic molecule, peptide, peptide mimetic, protein (e.g. antibody, growth factor), an antigen or immunogen, mRNA, small interfering RNA (siRNA), or a polynucleotide, a virus, or a therapeutic agent. Organic or inorganic molecules can include, but are not limited to, a homogenous or heterogeneous mixture of compounds, including pharmaceuticals, radioisotopes, crude or purified plant extracts, and/or an entity that alters, inhibits, activates, or otherwise affects biological or biochemical events, including classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, cytokines, chemokines, etc.) that are commonly found in cells and tissues, whether the molecules themselves are naturally-occurring or artificially created (e.g., by synthetic or recombinant methods).

If mRNA is the cargo or active agent for example, the 3' end of the mRNA can be selectively thiolated by periodate oxidation followed by reductive amination with cysteine. Cationic DA nanogels may also complex with mRNA by electrostatics alone.

Examples of such agents include, but are not limited to, agents for gene therapy; analgesics; anti-arthritics; anti-asthmatic agents; anti-cancer agents; anti-cholinergics; anti-convulsants, anti-depressants; anti-diabetic agents; anesthetics; antibiotics; antigens; anti-histamines; anti-infectives; anti-inflammatory agents; anti-microbial agents; anti-fungal agents, anti-Parkinson agents; anti-spasmodics; anti-pruritics; anti-psychotics; anti-pyretics; anti-viral agents; nucleic acids; DNA; RNA; siRNA; polynucleotides, nucleosides; nucleotides; amino acids, peptides; proteins; carbohydrates; lectins; lipids; fats; fatty acids; viruses, immunogens; anti-bodies and fragments thereof, sera; immunostimulants; immunosuprressants; cardiovascular agents; channel blockers (e.g., potassium channel blockers, calcium channel blockers, beta-blockers, alpha-blockers), anti-arrhythmics; anti-hypertensives; inhibitors of DNA, RNA, or protein synthesis; neurotoxins; vasodilating agents; vasoconstricting agents; gases; growth factors; growth inhibitors; hormones, steroids; steroidal and non-steroidal anti-inflammatory agents; corticosteroids; angiogenic agents; anti-angiogenic agents, hypnotics; muscle relaxants; muscle contractants; sedatives; tranquilizers; ionized and non-ionized active agents; metals; small molecules, pharmaceuticals, hemotherapeutic agents; wound healing agents; indicators of change in the bio-environment; enzymes; enzyme inhibitors; nutrients; vitamins; minerals; coagulation factors; anticoagulants; anti-thrombotic agents, neurochemicals (e.g., neurotransmitters); cellular receptors; radioactive materials; contrast agents (e.g., fluorescence, magnetic, radioactive); nanoparticles (e.g., magnetic, semiconductor, dielectric, or metal); vaccines; modulators of cell growth; modulators of cell adhesion; cell response modifiers; cells; chemical or biological materials or compounds that induce a desired biological or pharmacological effect; and combinations thereof.

Throughout this specification, "comprise" or variations such as "comprises" or "comprising" imply the inclusion of a stated integer (or components) or group of integers (or components), but not the exclusion of any other integer (or component) or group of integers (or components).

The singular forms "a," "an," and "the" include the plurals unless the context clearly dictates otherwise.

"Including" means "including but not limited to." "Including" and "including but not limited to" are used interchangeably.

"Pharmaceutically acceptable carrier" refers to a non-toxic carrier that may be administered to a patient-together with compositions described herein—and which does not destroy the pharmacological activity of the active agents within the composition. "Excipient" refers to an additive in a formulation or composition that is not a pharmaceutically active ingredient.

"Pharmaceutically effective amount" refers to an amount effective to treat a patient, e.g., effecting a beneficial and/or desirable alteration in the general health of a patient suffering from a disease or condition (including but not limited cancer). Treating includes, but is not limited to, killing cells, preventing the growth of new cells, improving vital functions of a patient, improving the well-being of the patient, decreasing pain, improving appetite, improving patient weight, and any combination thereof. A "pharmaceutically effective amount" also refers to the amount required to improve a patient's clinical symptoms.

"Peptide" and "polypeptide" are used synonymously herein to refer to polymers constructed from amino acid residues. "Amino acid residue" as used herein refers to any naturally occurring amino acid (L or D form), non-naturally occurring amino acid, or amino acid mimetic (such as peptide monomer).

"Identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity for purposes of the present disclosure is determined using the BLAST algorithm, described in Altschul et al. (1990) *J. Mol. Biol.* 215:403-10. This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., (1990) *J. Mol. Biol.* 215:403-10). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence the BLASTP settings are: word length (W), 3; expectation (E), 10; and the BLOSUM62 scoring matrix. For analysis of nucleic acid sequences, the BLASTN program settings are word length (W), 11; expectation (E), 10; M=5; N=−4; and a comparison of both strands. The TBLASTN program (using a protein sequence to query nucleotide sequence databases) uses a word length (W) of 3, an expectation (E) of 10, and a BLOSUM 62 scoring matrix. (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01.

The "length" of a polypeptide is the number of amino acid residues linked end-to-end that constitute the polypeptide, excluding any non-peptide linkers and/or modifications that the polypeptide may contain.

Hydrophobic amino acid residues are characterized by a functional group ("side chain") that has predominantly non-polar chemical properties. Such hydrophobic amino acid residues can be naturally occurring (L or D form) or non-naturally occurring. Alternatively, hydrophobic amino acid residues can be amino acid mimetics characterized by a side chain that has predominantly non-polar chemical properties. Conversely, hydrophilic amino acid residues are characterized by a side chain that has predominantly polar (charged or uncharged) chemical properties. Such hydrophilic amino acid residues can be naturally occurring (L or D form) or non-naturally occurring. Alternatively, hydrophilic amino acid residues can be amino acid mimetics characterized by a side chain that has predominantly polar (charged or uncharged) chemical properties. Suitable non-naturally occurring amino acid residues and amino acid mimetics are known in the art. See, e.g., Liang et al. (2013) *PLOS ONE* 8 (7):e67844.

Although most amino acid residues can be considered as either hydrophobic or hydrophilic, a few-depending on their context—can behave as either hydrophobic or hydrophilic. For example, the relatively weak non-polar characteristics of glycine, proline, and cysteine enable them each sometimes to function as hydrophilic amino acid residues. Conversely, the bulky, slightly hydrophobic side chains of histidine and arginine enable them each sometimes to function as hydrophobic amino acid residues.

Unless otherwise specified, each embodiment disclosed herein may be used alone or in combination with any one or more other embodiments herein.

"Transfection" refers to introduction of foreign nucleic acid into eukaryotic cells. Transfection may be accomplished by a variety of means known to the art, including electroporation, polymers (nanoparticles), calcium phosphate-DNA co-precipitation, DEAE-dextran-mediated transfection, polybrene-mediated transfection, microinjection, liposome fusion, lipofection, protoplast fusion, and biolistics.

"Stable transfection" or "stably transfected" refers to the introduction and integration of foreign nucleic acid, DNA, into the genome of the transfected cell.

The term variant refers to a protein, or fragment thereof, having an amino acids sequence that is similar, but not identical, to a referenced sequence (e.g., a SARS-CoV-2 protein sequence), wherein the activity of the variant protein is not significantly altered. These variations in sequence can be naturally occurring variations or they can be engineered through the use of technique known to those skilled in the art. Examples of suitable variations include, but are not limited to, amino acid deletions, insertions, substitutions, and combinations thereof.

Amino acids can be classified into groups based on their physical properties. Examples of such groups include, but are not limited to, charged amino acids, uncharged amino acids, polar uncharged amino acids, and hydrophobic amino acids. Preferred variants are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class.

The terms subject, patient, individual, etc. are not intended to be limiting and can be generally interchanged. That is, an individual described as a patient does not necessarily have a given disease, but may be merely seeking medical advice. As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient, individual and subject may be used interchangeably and these terms are not intended to be limiting. That is, an individual described as a patient does not necessarily have a given disease, but may be merely seeking medical advice. The terms patient or subject include human and veterinary subjects.

Reference herein to "therapeutic" and "prophylactic" is to be considered in their broadest contexts. "Therapeutic" does not necessarily imply that a mammal is treated until total recovery. Similarly, "prophylactic" does not necessarily mean that the subject will not eventually contract a disease condition. The term "prophylaxis" may be considered as reducing the severity of onset of a particular condition. Therapy may also reduce the severity of an existing condition or the frequency of acute attacks. As used herein, "treat," "treating," and similar words mean stabilizing and/or reducing the symptoms of a disease or condition. In some aspects, the compositions disclosed herein can prevent the occurrence of a disease or condition, or cure a medical condition or disease, which is separate from treating.

Routes and frequency of administration of the therapeutic compositions described herein, as well as dosage, will vary from individual to individual, and from disease to disease, and may be readily established using standard techniques. In general, the pharmaceutical compositions may be administered by injection (e.g., intracutaneous, intramuscular, intravenous or subcutaneous), intranasally (e.g., by aspiration), in pill form (e.g. swallowing, suppository for vaginal or rectal delivery).

According to the methods provided herein, the subject is administered an effective amount or therapeutically effective amount of one or more of the agents provided herein. The terms effective amount, therapeutically effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are hose large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 22nd Edition, Gennaro, Editor (2012), and Pickar, Dosage Calculations (1999)).

Compositions suitable for injectable use include sterile aqueous solutions (where water soluble) and sterile powders for the extemporaneous preparation of sterile injectable solutions. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like.

In conjunction with any of the foregoing methods, the compositions can be administered in combination with another drug. In each case, the composition can be administered prior to, at the same time as, or after the administration of the other drug. In accordance with the methods described herein, more than one compound or composition may be co-administered with one or more other compounds, such as known chemotherapies, anti-viral compounds or molecules as well as antibiotics, chloroquine, hydroxychloroquine, known drugs for treating pneumonia, an analgesic (such as lidocaine or paracetoamol), an anti-inflammatory (such as betamethasone, non-steroid anti-inflammatory drugs (NSAIDs), acetaminophen, ibuprofen, naproxen), and/or other suitable drugs. The provided methods may be further combined with other tumor therapies such as radiotherapy, surgery, hormone therapy and/or immunotherapy. Thus, the provided methods can further include administering one or more additional therapeutic agents to the subject. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated. Optionally, the additional therapeutic agent is octreotide acetate, interferon, pembrolizumab, glucopyranosyl lipid A, carboplatin, etoposide, or any combination thereof.

"Co-administered" conveys simultaneous administration in the same formulation or in two different formulations via the same or different routes or sequential administration by the same or different routes. "Sequential" administration conveys a time difference of seconds, minutes, hours, or days between the administration of the two or more separate compounds In some embodiments, it may be beneficial to include one or more excipients in a composition. One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to determine empirically which excipients, if any, to include in the formulations or compositions disclosed herein. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier.

In some embodiments, it may be beneficial to include a solubilizing agent. Solubilizing agents may be useful for increasing the solubility of any of the components of the formulation or composition, including a peptide disclosed herein or an excipient. The solubilizing agents described herein are not intended to constitute an exhaustive list, but are provided merely as exemplary solubilizing agents that may be used. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

The pH may be any pH that provides desirable properties for the composition. Desirable properties may include, for example, peptide stability, increased peptide retention as compared to compositions at other pHs, and improved filtration efficiency.

In some embodiments, it may be beneficial to include a tonicity-adjusting agent. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list but are provided merely as exemplary tonicity-adjusting agents that may be used. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

In some embodiments, it may be beneficial to include a stabilizing agent. Stabilizing agents help increase the stability of peptides in compositions of the invention.

In some embodiments, it may be beneficial to include a protectant. Protectants are agents that protect a pharmaceutically active ingredient (e.g., a peptide as disclosed herein) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., a peptide as disclosed herein) when a formulation is exposed to a temperature below its freezing point. For example, a cryoprotectant could be included in a reconstituted lyophilized formulation so that the formulation could be frozen before dilution for intravenous (IV) administration. Cryoprotectants are well known in the art. Accordingly, the cryoprotectants described herein are not intended to constitute an exhaustive list, but are provided merely as exemplary cryoprotectants that may be used. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol, propylene glycol).

Lyoprotectants are useful in stabilizing the components of a lyophilized formulation or composition. For example, a peptide as disclosed herein could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used. Lyoprotectacts include, but are not limited to, solvents, surfactants, encapsulating agents, stabilizing agents, viscosity modifiers, and combinations thereof. Exemplary lyoprotectants may be, for example, sugars and polyols, trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list but are provided merely as exemplary antioxidants that may be used. Antioxidants may be, for example, sodium ascorbate, citrate, thiols, metabisulfite, and combinations thereof.

Variations, modifications, and other implementations of what is described herein will occur to those of ordinary skill without departing from the spirit and the scope of the present disclosure. Accordingly, the ensuing claims not to be limited only to the preceding illustrative description.

Each of the embodiments described herein may be combined individually or in combination with one or more other embodiments of the invention.

Those skilled in the art will recognize or be able to ascertain using no more than routine experimentation, numerous equivalents to the compounds, compositions, and methods of use thereof described herein. Such equivalents are considered to be within the scope of the compositions and methods disclosed herein.

The contents of all references, patents and published patent applications cited throughout this Application, as well as their associated figures are hereby incorporated by reference in their entirety.

EXAMPLES

The following examples are put forth to provide those of ordinary skill in the art with a complete disclosure and description of how to make and use the embodiments and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1: Mannan Nanogel Synthesis Protocol (4 Days)

A. Mannan and Dextran Oxidation and Purification:
Materials: Mannan; FITC Dextran; 100 mM Sodium acetate (NaOAc buffer, pH 5.5); PD 10 Desalting Column; CENTRI-SEP™ columns (Princeton Separations); sodium periodate (NaIO4); SPIN-X® 10k MWCO Concentrator (Corning)
Preparation:
For each mannan oxidation to be performed, one PD 10 desalting column is prepared by pouring off the buffer in the top portion, cutting off the bottom tip, and mounting it on a clamp stand. The column is primed by filling the top with NaOAc buffer 4 times, letting it drain completely after each fill.

If fluorescent dextran is to be oxidized, one CENTRI-SEP™ column is prepared for every 500 µg of oxidized dextran required by adding 800 µL of NaOAc buffer to each column and vortexing thoroughly.
Oxidation:
Mannan is weighed out (>15 mg per oxidation to be performed) directly into a 5 mL tube and dissolve in NaOAc buffer to a concentration of 10 mg/mL. NaIO4 is weighed out to make a solution volume equal to the volume of the mannan solution. The concentration of NaIO4 is 120 mM for oxidizing mannan for nanogel core formation and 2 mM for oxidizing mannan for secondary mannan addition. The NaIO4 is dissolved in the NaOAc buffer.

For each oxidation to be performed, 1.5 mL of the mannan solution is mixed with 1.5 mL of the appropriate NaIO4 solution in a 5 mL tube. Final NaIO4 concentration=60 mM for core formation and 1 mM for secondary mannan If oxidized fluorescent dextran is to be prepared, a 10 mg/mL solution is made in NaOAc buffer and for every 500 µg of oxidized dextran required, 60 µL of dextran solution is mixed with 60 µL of 120 mM NaIO4 solution in a tube.

The tubes are wrapped in foil and reacted for 30 min with rotation.
Purification:
Each oxidized mannan (ox-man) reaction solution is added to it's own PD 10 desalting column and allowed to drain completely into waste. A SPIN-X® concentrator is placed under each column and the purified mannan is eluted into the concentrator by adding 3.5 mL of NaOAc buffer to the column and letting it drain completely. The concentrator is then spun 4k×g for 13 min.

All of the mannan from the top portion of the concentrator is transferred to a 1.7 mL tube and the total volume is brought up to 1.25 mL by measuring the starting volume with a 1 mL pipette and adding NaOAc buffer. This is 10 mg/mL assuming zero-lose.

The CENTRI-SEP™ column(s) are drained for dextran purification by removing the top and bottom caps, the column bed is set by spinning at 800×g for 2 min. 100 µL of dextran reaction solution is then added to each column bed nested in a clean 1.7 mL tube and spun again at 800×g for 2 min.~90 µL will elute, which means the concentration is ~5.6 mg/mL assuming zero-lose.

Store the purified oxidized mannan or dextran at 4° C. if not used immediately.
B. Mannan Self-Assembly:
Materials: Aniline
Preparation of 500 µg Nanogel (NG) Batches:
A total of 500 µg (assuming zero-lose) of oxidized mannan and dextran is added to a 1.7 mL tube for each batch. 5 µL of aniline is added to each tube and then the tube is shaken immediately. Bath sonicate all tubes for about 10 sec each, then leave under foil overnight.

C. Nanogel Cross-Linking

Materials: Succinic dihydrazide (SDH); 3,3'-Dithiobis (propanoic dihydrazide; DPDH); Cystamine dihydrochloride ("Cystamine"); ethylenediamine dihydrochloride (EDA); sodium cyanoborohydride (NaCNBH$_3$); acetonitrile (ACN); 100 mM Sodium acetate, pH 5.5 (NaOAc buffer); PBS (never DPBS); 1 normal (molar) sodium hydroxide (1N NaOH)

Dihydrazide (DH) Crosslinking:

Bath sonicate all tubes to ensure a good pellet upon spin. The nanogels (NG) from section B above are spun at 15k×g for 4 min. The supernatant is aspirated with pipette, 1 mL NaOAc buffer is added and the NG is resuspended using short pulses from a probe sonicator. The NG is spun and resuspend in 1 mL of 2:1 (vol) ACN:NaOAc with 50 mM SDH and 50 mM DPDH. React under foil overnight with rotation.

Diamine (DA) Crosslinking:

Bath sonicate all tubes to ensure a good pellet upon spin. The nanogels (NG) from section B above are spun and washed with 1 mL NaOAc buffer and then spun and resuspended in 1 mL of PBS with 50 mM EDA and 50 mM cystamine. Allow to react for 1 hr under foil with rotation. A 5M solution of NaCNBH$_3$ in 1N NaOH is prepared and then 20 µL of this solution is added to each NG tube. React overnight under foil with rotation.

Storage for Later Use:

After reaction overnight at room temp, DH crosslinked NGs can be stored as-is at 4° C. for later use.

Prior to storage at 4° C., DA crosslinked NGs must be washed once with 1 mL PBS then resuspended in 1 mL PBS.

D. Secondary Mannan Treatment:

Materials: 1 mM ox-man (10 mg/mL) from Section A; aniline; NaOAc buffer (100 mM Sodium acetate, pH 5.5); PBS; Sodium cyanoborohydride (NaCNBH$_3$)

Secondary Mannan Addition to DH Crosslinked NGs:

Bath sonicate all tubes to ensure a good pellet upon spin. The NGs (still in DH solution) are spun and washed with 1 mL of 2:1 (vol) ACN:NaOAc. Each NG batch is resuspended in 1 mL of NaOAc buffer. Each tube is then split into 2 new tubes with 500 µL (250 µg ox-man) in each. All prepared samples may be pooled prior to splitting. All subsequent steps will be for this 250 µg half-batch size.

Each new tube is spun and resuspended in 50 µL 1 mM ox-man+350 µL NaOAc buffer and reacted overnight under foil.

Secondary Mannan Addition to DA Crosslinked NG:

Bath sonicate all tubes to ensure a good pellet upon spin. The NGs (already washed and in 1 mL PBS) are split into 2 new tubes with 500 µL (250 µg ox-man) in each. All prepared samples may be pooled prior to splitting. All subsequent steps will be for this 250 µg half-batch size.

Each new tube is spun and resuspended in 50 µL 1 mM ox-man+350 µL PBS and reacted for 1 hr under foil. A 5M solution of NaCNBH$_3$ in 1N NaOH is prepared. 10 µL of this solution is added to each NG tube and reacted overnight under foil.

E. Activation and Cargo Loading:

Materials: PBS; tris(2-carboxyethyl) phosphine (TCEP); 18MΩ dionized water (DI); 100% methanol (MeOH); sodium borohydride (NaBH4); 2,2-dithiopyridine (DTP); glacial acetic acid (AcOH); glutathione, reduced (GSH); dimethylsulfoxide (DMSO); 10 normal (molar) sodium hydroxide (10N NaOH); peptides.

Reduce Disulfide Crosslinks to Thiols with TCEP:

Bath sonicate all tubes to ensure a good pellet upon spin. A 100 mM solution of TCEP is prepared in PBS, then for every 10 mL, 350 µL of 10N NaOH is added to this solution. Confirm a pH between 6.9 and 7.5. The NGs (DH and DA NGs treated (almost) identically in subsequent steps) are spun and resuspend in 1 mL of TCEP solution and reacted for 1 hr under foil with rotation.

Reduce imines and residual aldehydes with borohydride (This step can be skipped for DA crosslinked NG, but will not harm them):

The NGs are washed once with 1 mL DI and once with 1 mL MeOH. The NGs are resuspended in 1 mL of 100 mM NaBH4 in MeOH. React for 1 hr.

Activate Thiols with DTP:

The NGs are washed with 1 mL MeOH (if skipping step above, first wash with 1 mL DI) and resuspend in 100 mM DTP in 160:1 MeOH:AcOH. React for 4 hr under foil with rotation.

Load Thiol Cargo (Cargo Will Vary Frequently by Experiment):

The cargo solution is prepared cargo solution by dissolving GSH to 200 mM in DI, then diluting to 20 mM with DMSO. The peptides are dissolved to 20 mM in DMSO. Some peptides may require 200 mM dissolution in either DI or other solvent. The NGs are washed with 1 mL MeOH. A total of 100 µL of 20 mM cargo solution is added to each tube, then 900 µL MeOH is added and resuspend. React overnight under foil with rotation.

Preparation for Delivery:

The NGs are washed once with MeOH and once with DI and the resuspend in either 200 µL (=1000× concentration) or 1 mL (200× concentration) of sterile PBS and resuspend with the bath sonicator (~30 s-1 min).

Example 2: Nanogel-RNA Delivery by Attachment of Thiol-Modified RNA Via Disulfide Linking A. Materials: tris(2-carboxyethyl) phosphine (TCEP); 100 mM Sodium acetate (NaOAc buffer, pH 5.5); CENTRI-SEP™ columns (Princeton Separations); Sodium periodate (NaIO4); Sodium cyanoborohydride (NaCNBH$_3$); Cystamine dihydrochloride ("Cystamine"); phosphate buffer saline (PBS, pH 7.4); 1 normal (molar) sodium hydroxide (1N NaOH)

B. RNA 3' Oxidation:

50 µL of RNA at 10 mg/mL is mixed with a 50 µL of a 20 mM solution of NaIO4 in NaOAc buffer, and reacted under foil for 30 min. The oxidized RNA is purified using a CENTRI-SEP™ column into PBS.

C. Reductive Amination of RNA 3' Aldehydes:

10 µL of 100 mM cystamine in PBS is added to the oxidized RNA and reacted for 1 hr. 1 µL of a 5M solution of NaCNBH$_3$ in 1N NaOH is then added and reacted for 2 hrs. The oxidized RNA is purified using a CENTRI-SEP™ column into PBS.

D. Reduction with TCEP to Expose RNA 3' Thiols:

10 µL of 100 mM TCEP in PBS (pH~7) is added to the cystamine-modified RNA and reacted for 1 hr. The oxidized RNA is purified using a CENTRI-SEP™ column into PBS.

E. RNA-Nanogel Linking/Complexation:

A suspension of mannan nanogels is added in the DTP-activated state (see nanogel protocol in Example 1) in PBS into a solution of 2 µg of thiol-modified RNA to a total volume of 200 µL. (The amount of nanogels used can be varied to achieve different nanogel:RNA ratios. A wt:wt ratio of ~25 achieved the highest expression.) The mixture is then vortexed on high for ~30 s and left to react overnight under foil.

Example 3: Nanogel-RNA Delivery by Electrostatic Complexation of RNA with Nanogels RNA-Nanogel Complexation:

A suspension of DiAm (cationic) mannan nanogels is added in the DTP-activated state (see nanogel protocol in Example 1) in PBS into a solution of 2 μg of unmodified RNA to a total volume of 200 μL. (The amount of nanogels used can varied to achieve different nanogel:RNA ratios. A wt:wt ratio of ~25 achieved the highest expression.) The mixture is vortexed on high for ~30 s and left to react for 15 min.

Example 4: Method for CD206 Expressing 293T Cell

A CMV promoter driven CD206 expression plasmid was constructed with a codon optimized CD206 sequence and Puromycin resistance gene. 293T cells were transfected with the CD206 expression plasmid with Lipofectamine 2000 using the manufacturer's recommended conditions and placed under selection with Puromycin for 2 weeks. Single CD206 positive cells were cultured into 96 well plate using a cell sorter, and 293T clones exhibiting CD206 expression were selected.

What is claimed is:

1. A method of making a self-assembling mannan nanogel for in vivo delivery of therapeutic agents, the method comprising:
   a. oxidizing mannan with periodate (NaIO4);
   b. purifying the oxidized mannan;
   c. adding aniline to the purified oxidized mannan to produce a mannan derivative with hydrophobic phenylimine groups covalently attached to the mannan, wherein the mannan derivative self-assembles into a mannan nanogel;
   d. further reacting the mannan nanogel with succinate dihydrazide (SDH) and 3,3'-Dithiobis(propanoic dihydrazide) (DPDH), thereby introducing dihydrazide crosslinkers into the self-assembled mannan nanogel;
   e. further reducing the mannan nanogel disulfide crosslinks with (tris(2-carboxyethyl) phosphine) (TCEP);
   f. reducing imines and residual aldehydes in the mannan nanogel with borohydride (NaBH4); and
   g. activating thiols in the mannan nanogel with 2,2-dithiopyridine (DTP), thereby preparing the mannan nanogel for loading with thiol-containing cargo.

2. The method of claim 1, wherein the thiol-containing cargo is loaded onto the DTP-activated nanogel, wherein the cargo is comprised of one or more peptides.

3. The method of claim 1, wherein dihydrazide cross-linked nanogels are coated with NaIO4-oxidized mannan.

4. The method of claim 1, wherein the thiol-containing cargo is loaded into the DTP-activated nanogel, wherein the cargo is comprised of one or more peptides, and optionally glutathione (GSH).

5. The method of claim 1, wherein the thiol-containing cargo is loaded into the DTP-activated nanogel, wherein the cargo is comprised of one or more viral antigens.

6. The method of claim 1, wherein the thiol-containing cargo is loaded into the DTP-activated nanogel, wherein the cargo is comprised of one or more nucleic acids.

7. The method of claim 6, wherein the nucleic acids are comprised of thiolated mRNA.

* * * * *